(12) United States Patent
Umbarger

(10) Patent No.: US 9,115,387 B2
(45) Date of Patent: Aug. 25, 2015

(54) METHODS FOR ANALYZING NUCLEIC ACIDS

(71) Applicant: Good Start Genetics, Inc., Cambridge, MA (US)

(72) Inventor: Mark Umbarger, Brookline, MA (US)

(73) Assignee: Good Start Genetics, Inc., Cambridge, MA (US)

( * ) Notice: Subject to any disclaimer, the term of this patent is extended or adjusted under 35 U.S.C. 154(b) by 0 days.

(21) Appl. No.: 14/313,234

(22) Filed: Jun. 24, 2014

(65) Prior Publication Data

US 2014/0308667 A1  Oct. 16, 2014

Related U.S. Application Data

(63) Continuation of application No. 14/210,776, filed on Mar. 14, 2014, now Pat. No. 8,778,609.

(60) Provisional application No. 61/784,624, filed on Mar. 14, 2013.

(51) Int. Cl.
 *C12Q 1/68* (2006.01)
 *C12P 19/34* (2006.01)

(52) U.S. Cl.
 CPC ............ *C12Q 1/6813* (2013.01); *C12Q 1/6837* (2013.01); *C12Q 1/6874* (2013.01)

(58) Field of Classification Search
 None
 See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,988,617 A | 1/1991 | Landegren et al. |
| 5,234,809 A | 8/1993 | Boom et al. |
| 5,242,794 A | 9/1993 | Whiteley et al. |
| 5,494,810 A | 2/1996 | Barany et al. |
| 5,583,024 A | 12/1996 | McElroy et al. |
| 5,604,097 A | 2/1997 | Brenner |
| 5,636,400 A | 6/1997 | Young |

(Continued)

FOREIGN PATENT DOCUMENTS

| | | |
|---|---|---|
| EP | 1321477 A1 | 6/2003 |
| EP | 1564306 A2 | 8/2005 |

(Continued)

OTHER PUBLICATIONS

Fan et al., "Highly Parallel SNP Genotyping," Cold Spring Harb. Symp. Quant. Biol. 2003, 68:69-78.*

(Continued)

*Primary Examiner* — Samuel Woolwine
*Assistant Examiner* — Kaijiang Zhang
(74) *Attorney, Agent, or Firm* — Thomas C. Meyers; Brown Rudnick LLP

(57) ABSTRACT

The invention generally relates to methods for analyzing nucleic acids. In certain aspects, methods of the invention involve obtaining a sample including a nucleic acid template. A plurality of molecular inversion probes are tiled across a portion of the template. The probes are designed such that immediately adjacent probes hybridize to opposite strands of the nucleic acid template and probes on the same strand hybridize to the template in an overlapping manner. A region between targeting arms of a plurality of the molecular inversion probes is filled-in with nucleotides, and the filled-in region of a plurality of the probes is analyzed to obtain sequence information about the nucleic acid template.

15 Claims, 1 Drawing Sheet

(56) References Cited

U.S. PATENT DOCUMENTS

| | | |
|---|---|---|
| 5,674,713 A | 10/1997 | McElroy et al. |
| 5,695,934 A | 12/1997 | Brenner |
| 5,700,673 A | 12/1997 | McElroy et al. |
| 5,701,256 A | 12/1997 | Marr et al. |
| 5,830,064 A | 11/1998 | Bradish et al. |
| 5,846,719 A | 12/1998 | Brenner et al. |
| 5,863,722 A | 1/1999 | Brenner |
| 5,866,337 A | 2/1999 | Schon |
| 5,869,252 A | 2/1999 | Bouma et al. |
| 5,871,921 A | 2/1999 | Landegren et al. |
| 5,993,611 A | 11/1999 | Moroney, III et al. |
| 6,100,099 A | 8/2000 | Gordon et al. |
| 6,138,077 A | 10/2000 | Brenner |
| 6,150,516 A | 11/2000 | Brenner et al. |
| 6,172,214 B1 | 1/2001 | Brenner |
| 6,172,218 B1 | 1/2001 | Brenner |
| 6,197,508 B1 | 3/2001 | Stanley |
| 6,210,891 B1 | 4/2001 | Nyren et al. |
| 6,223,128 B1 | 4/2001 | Allex et al. |
| 6,235,472 B1 | 5/2001 | Landegren et al. |
| 6,235,475 B1 | 5/2001 | Brenner et al. |
| 6,235,501 B1 | 5/2001 | Gautsch et al. |
| 6,258,568 B1 | 7/2001 | Nyren |
| 6,274,320 B1 | 8/2001 | Rothberg et al. |
| 6,306,597 B1 | 10/2001 | Macevicz |
| 6,352,828 B1 | 3/2002 | Brenner |
| 6,361,940 B1 | 3/2002 | Van Ness et al. |
| 6,403,320 B1 | 6/2002 | Read et al. |
| 6,489,105 B1 | 12/2002 | Matlashewski et al. |
| 6,558,928 B1 | 5/2003 | Landegren |
| 6,582,938 B1 | 6/2003 | Su et al. |
| 6,714,874 B1 | 3/2004 | Myers et al. |
| 6,719,449 B1 | 4/2004 | Laugharn, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,858,412 B2 | 2/2005 | Willis et al. |
| 6,911,345 B2 | 6/2005 | Quake et al. |
| 6,913,879 B1 | 7/2005 | Schena |
| 6,948,843 B2 | 9/2005 | Laugharn, Jr. et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,264,929 B2 | 9/2007 | Rothberg et al. |
| 7,282,337 B1 | 10/2007 | Harris |
| 7,297,518 B2 | 11/2007 | Quake et al. |
| 7,320,860 B2 | 1/2008 | Landegren et al. |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,666,593 B2 | 2/2010 | Lapidus |
| 7,700,323 B2 | 4/2010 | Willis et al. |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng et al. |
| 7,865,534 B2 | 1/2011 | Chandra et al. |
| 7,883,849 B1 | 2/2011 | Dahl |
| 7,957,913 B2 | 6/2011 | Chinitz et al. |
| 7,960,120 B2 | 6/2011 | Rigatti et al. |
| 7,993,880 B2 | 8/2011 | Willis et al. |
| 8,024,128 B2 | 9/2011 | Rabinowitz et al. |
| 8,165,821 B2 | 4/2012 | Zhang |
| 8,209,130 B1 | 6/2012 | Kennedy et al. |
| 2001/0007742 A1 | 7/2001 | Landergren |
| 2001/0046673 A1 | 11/2001 | French et al. |
| 2002/0001800 A1 | 1/2002 | Lapidus |
| 2002/0164629 A1 | 11/2002 | Quake et al. |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0177105 A1 | 9/2003 | Xiao et al. |
| 2003/0203370 A1 | 10/2003 | Yakhini et al. |
| 2003/0224384 A1 | 12/2003 | Sayood et al. |
| 2004/0106112 A1 | 6/2004 | Nilsson et al. |
| 2004/0142325 A1 | 7/2004 | Mintz et al. |
| 2004/0152108 A1 | 8/2004 | Keith et al. |
| 2004/0209299 A1 | 10/2004 | Pinter et al. |
| 2005/0026204 A1 | 2/2005 | Landegren |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boom et al. |
| 2005/0244879 A1 | 11/2005 | Schumm et al. |
| 2006/0019304 A1 | 1/2006 | Hardenbol et al. |
| 2006/0024681 A1 | 2/2006 | Smith et al. |
| 2006/0078894 A1 | 4/2006 | Winkler et al. |
| 2006/0177837 A1 | 8/2006 | Borozan et al. |
| 2006/0183132 A1 | 8/2006 | Fu et al. |
| 2006/0192047 A1 | 8/2006 | Goossen |
| 2006/0292585 A1 | 12/2006 | Nautiyal et al. |
| 2006/0292611 A1 | 12/2006 | Berka et al. |
| 2007/0020640 A1 | 1/2007 | McCloskey et al. |
| 2007/0042369 A1 | 2/2007 | Reese et al. |
| 2007/0092883 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0166705 A1 | 7/2007 | Milton et al. |
| 2007/0225487 A1 | 9/2007 | Nilsson et al. |
| 2007/0264653 A1 | 11/2007 | Berlin et al. |
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0269068 A1 | 10/2008 | Church et al. |
| 2008/0280955 A1 | 11/2008 | McCamish |
| 2008/0293589 A1 | 11/2008 | Shapero |
| 2009/0019156 A1 | 1/2009 | Mo et al. |
| 2009/0026082 A1 | 1/2009 | Rothberg et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0191565 A1 | 7/2009 | Lapidus et al. |
| 2009/0192047 A1 | 7/2009 | Parr et al. |
| 2009/0203014 A1 | 8/2009 | Wu et al. |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0188073 A1 | 7/2010 | Rothberg et al. |
| 2010/0197507 A1 | 8/2010 | Rothberg et al. |
| 2010/0216151 A1 | 8/2010 | Lapidus et al. |

(56) References Cited

U.S. PATENT DOCUMENTS

| | | |
|---|---|---|
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | Mckernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0034342 A1 | 2/2011 | Fox |
| 2011/0098193 A1 | 4/2011 | Kingsmore et al. |
| 2011/0159499 A1 | 6/2011 | Hindson et al. |
| 2011/0166029 A1 | 7/2011 | Margulies et al. |
| 2011/0230365 A1 | 9/2011 | Rohlfs et al. |
| 2011/0257889 A1 | 10/2011 | Klammer et al. |
| 2011/0301042 A1 | 12/2011 | Steinmann et al. |
| 2012/0015050 A1 | 1/2012 | Abkevich et al. |
| 2012/0021930 A1 | 1/2012 | Schoen et al. |
| 2012/0059594 A1 | 3/2012 | Hatchwell et al. |
| 2012/0164630 A1 | 6/2012 | Porreca et al. |
| 2012/0165202 A1 | 6/2012 | Porreca et al. |
| 2012/0179384 A1 | 7/2012 | Kuramitsu et al. |
| 2012/0252020 A1 | 10/2012 | Shuber |
| 2012/0252684 A1 | 10/2012 | Selifonov et al. |
| 2013/0275103 A1 | 10/2013 | Struble et al. |
| 2013/0344096 A1 | 12/2013 | Chiang et al. |

FOREIGN PATENT DOCUMENTS

| | | |
|---|---|---|
| EP | 2437191 A2 | 4/2012 |
| WO | 95/11995 A1 | 5/1995 |
| WO | 96/19586 A1 | 6/1996 |
| WO | 98/14275 A1 | 4/1998 |
| WO | 98/44151 A1 | 10/1998 |
| WO | 00/18957 A1 | 4/2000 |
| WO | 0293453 A2 | 11/2002 |
| WO | 2004/018497 | 3/2004 |
| WO | 2004/083819 A2 | 9/2004 |
| WO | 2005/003304 A2 | 1/2005 |
| WO | 2007/010251 A2 | 1/2007 |
| WO | 2007/107717 A1 | 9/2007 |
| WO | 2007/123744 | 11/2007 |
| WO | 2007/135368 A2 | 11/2007 |
| WO | 2009/036525 A2 | 3/2009 |
| WO | 2010024894 A1 | 3/2010 |
| WO | 2010126614 A2 | 11/2010 |
| WO | WO 2010126614 A2 * | 11/2010 |
| WO | 2012040387 A1 | 3/2012 |
| WO | 2012/051208 A2 | 4/2012 |
| WO | 2012/087736 A1 | 6/2012 |
| WO | 2012/109500 A2 | 8/2012 |
| WO | 2012/134884 A1 | 10/2012 |
| WO | 2013/058907 A1 | 4/2013 |

OTHER PUBLICATIONS

Chevreux, B., et al., 1999, Genome Sequence Assembly Using Trace Signals and Additional Sequence Information, Computer Science and Biology: Proceedings of the German Conference on Bioinformatics (GCB) 99:45-56.

Choe, et al., 2010, Novel CFTR Mutations in a Korean Infant with Cystic Fibrosis and Pancreatic Insufficiency, J Korean Med Sci 25:163-5.

Ciotti, et al., 2004, Triplet Repeat Primed PCR (TP PCR) in Molecular Diagnostic Testing for Friedrich Ataxia, Journal of Molecular Diagnostics 6(4):285-9.

Collins, et al., 2004, Finishing the euchromatic sequence of the human genome, Nature 431.7011:931-45.

Dahl, et al., 2005, Multiplexamplification enabled by selective circularization of large sets of genomic DNA fragments, Nucleic Acids Research 33:e71.

de la Bastide, M. & McCombie, 2007, W. R., Assembling genome DNA sequences with PHRAP, Current Protocols in Bioinformatics, 17:11.4.1-11.4.15.

Delcher, A.L., et al., 1999, Alignment of whole genomes, Nucleic Acids Research, 27:11.

DiGuistini, S., et al., 2009, De novo genome sequence assembly of a filamentous fungus using Sanger, 454 and Illumina sequence data, Genome Biology, 10:R94.

Dong, C. & Yu, B., 2011, Mutation Surveyor: An In Silico Tool for Sequencing Analysis, Methods in Molecular Biology 760:223-37.

Dore, et al., 1969, The Alkaline Denaturation of DNA, Biophysical Journal 9(11):1281-1311.

Dudley, et al., 2009, A Quick Guide for Developing Effective Bioinformatics Programming Skills, PLOS Comput Biol 5(12):e1000589.

Faulstich, et al., 1997, A sequencing method for RNA oligonucleotides based on mass spectrometry, Anal Chem 69:4349-4353.

Fares, et al., 2008, Carrier frequency of autosomal-recessive disorders in the Ashkenazi Jewish population: should the rationale for mutation choice for screening be reevaluated?, Prenatal Diagnosis 28:236-41.

Frey, Bruce, 2006, Statistics Hacks 108-115.

Friedenson, 2005, BRCA1 and BRCA2 Pathways and the Risk of Cancers Other Than Breast or Ovarian, Medscape General Medicine 7(2):60.

Gemayel, et al., 2010, Variable Tandem Repeats Accelerate Evolution of Coding and Regulatory Sequences, Annual Review of Genetics 44:445-77.

Glover, et al., 1995, Sequencing of oligonucleotides using high performance liquid chromatography and electrospray mass spectrometry, Rapid Com Mass Spec 9:897-901.

Gnirke, et al., 2009, Solution hybrid selection with ultra-long oligonucleotides for massively parallel targeted sequencing, nature biotechnology 27:182-9.

Goto, et al., 2010, BioRuby: bioinformatics software for the Ruby programming language, Bioinformatics 26(20):2617-9.

Hardenbol, et al., 2003, Multiplexed genotyping with sequence-tagged molecular inversion probes, nature biotechnology 21:673-8.

Harris, et al., 2006, Defects Can Increase the Melting Temperature of DNA-Nanoparticle Assemblies, The Journal of Physical Chemistry B 110:16393-6.

Hodges, et al., 2007, Genome-wide in situ exon capture for selective resequencing, nature genetics 29:1522-7.

Holland, et al., 2008, BioJava: an open-source framework for bioinformatics, Bioinformatics 24(18):2096-97.

Huang, et al., 2008, Comparative analysis of common CFTRpolymorphisms poly-T, TGrepeats and M470V in a healthy Chinese population, World J Gastroenterol 14(12):1925-30.

Husemann, P. & Stoye, 2009, Phylogenetic Comparative Assembly, Algorithms in Bioinformatics: 9th International Workshop, pp. 145-156, Salzberg, S., and Warnow, T., Eds. Springer-Verlag, Berlin Heidelberg.

Iqbal, et al., 2012, De novo assembly and genotyping of variants using colored de Bruijn graphs, Nature Genetics, 44 (2):226-233.

Jaijo, et al., 2010, Microarray-Based Mutation Analysis of 183 Spanish Families with Usher Syndrome, Investigative Ophthalmology & Visual Science 51(3):1311-7.

Jones, et al., 2008, Core Signaling Pathways in Human Pancreatic Cancers Revealed by Global Genomic Analyses, Science 321(5897):1801-1806.

Kent, W.J., 2002, BLAT—The Blast-like alignment tool, Genome Research 4: 656-664.

Kircher, et al., 2010, High-throughput DNA sequencing—concepts and limitations, Bioassays 32:524-36.

Kirpekar, et al., 1994, Matrix assisted laser desorption/ionization mass spectrometry of enzymatically synthesized RNA up to 150 kDa, Nucleic Acids Res 22:3866-3870.

(56) References Cited

OTHER PUBLICATIONS

Klein, et al., 2011, LOCAS—a low coverage assembly tool for resequence projects, PLoS One vol. 6, Issue 8, Document e23455, Aug. 15, 2011 (10 pages).
Krawitz, et al., 2010, Microindel detection in short-read sequence data, Bioinformatics 26(6).
Kreindler, J. L., 2010, Cystic fibrosis: Exploiting its genetic basis in the hunt for new therapies, Pharmacology and Therapeutics 125(2):219-29.
Kumar, S., et al., 2010, Comparing de novo assemblers for 454 transcriptome data, Genomics 11:571.
Kurtz, S., et al., 2004, Versatile and open software for comparing large genomes, Genome Biology, 5:R12.
Lam, et al., 2008, Compressed indexing and local alignment of DNA, Bioinformatics 24(6):791-97.
Langmead, et al., 2009, Ultrafast and memory-efficient alignment of short DNA sequences to the human genome, Genome Biology, 10:R25.
Larkin M.A., et al., 2007, Clustal W and Clustal X version 2.0, Bioinformatics, 23, 2947-2948.
Lecompte, O., et al., 2001, Multiple alignment of complete sequences (MACS) in the post-genomic era, Gene 270:17-30.
Li H. & Durbin R., 2009, Fast and accurate short read alignment with Burrows-Wheeler transform, Bioinformatics, 25 (14):1754-60.
Li H. & Durbin R., 2010, (2010) Fast and accurate long-read alignment with Burrows-Wheeler Transform. Bioinformatics, Epub.
Li, et al., 2008, SOAP: short oligonucleotide alignment program, Bioinformatics 24(5):713-14.
Li, et al., 2009, SOAP2: an improved ultrafast tool for short read alignment, Bioinformatics 25(15): 1966-67.
Li, et al., 2009, The Sequence Alignment/Map format and SAMtools, Bioinformatics, 2009, 25(16):2078-9.
Li, et al., 2011, Single Nucleotide Polymorphism Genotyping and Point Mutation Detection by Ligation on Microarrays, Journal of Nanoscience and Nanotechnology 11(2):994-1003.
Lin, et al., 2012, Development and evaluation of a reverse dot blot assay for the simultaneous detection of common alpha and beta thalassemia in Chinese, Blood Cells Molecules, and Diseases 48(2):86-90.
Lipman, D.J., et al., 1985, Rapid and sensitive protein similarity searches, Science 227(4693):1435-41.
Mamanova, 2010, Target-enrichment strategies for nextgeneration sequencing, Nature Methods 7(2):111-8.
Marras, 1999, Multiplex detection of single-nucleotide variations using molecular beacons, Genetic Analysis: Biomolecular Engineering 14:151.
May, Robert M., 1988, How Many Species Are There on Earth?, Science 241:1441.
Mills, R.E., et al., 2010, Mapping copy number variation by population-scale genome sequencing, Nature 470:59-65.
Minton, et al., 2011, Mutation Surveyor: Software for DNA Sequence Analysis, Methods in Molecular Biology 688:143-53.
Mockler, et al., 2005, Applications of DNA tiling arrays for whole-genome analysis, Genomics 85:1-15.
Mullan, L. J., 2002, Multiple sequence alignment—the gateway to further analysis, Brief Bioinform., 3:303-5.
Nan, et al., 2006, A novel CFTR mutation found in a Chinese patient with cystic fibrosis, Chinese Medical Journal 119(2):103-9.
Ng, et al., 2009, Targeted capture and massively parallel sequencing of 12 human exomes, Nature 461(7261):272-6.
Nicholas, H. B. Jr., et al., 2002, Strategies for multiple sequence alignment, Biotechniques 32:572-91.
Nilsson, et al., 2006, Analyzing genes using closing and replicating circles, Trends in Biotechnology 24:83-8.
Ning, Z., et al., 2001, SSAHA: a fast search method for large DNA databases, Genome Research 11(10): 1725-9 (2001).
Oka, et al., 2006, Detection of Loss of Heterozygosity in the p53 Gene in Renal Cell Carcinoma and Bladder Cancer Using the Polymerase Chain Reaction, Molecular Carcinogenesis 4(1).
Oliphant, et al., 2002, BeadArray?Technology: Enabling an Accurate, Cost-Effective Approach to High-Throughput Genotyping, Biotechniques Suppl:56-8, 60-1.
Ostrer, et al., 2001, A genetic profile of contemporary Jewish populations, Nature Reviews Cancer 2:891-8.
Owens, et al., 1998, Aspects of oligonucleotide and peptide sequencing with MALDI and electrospray mass spectrometry, Bioorg Med Chem 6:1547-1554.
Parameswaran, et al., 2007, A pyrosequencing-tailored nucleotide barcode design unveils opportunities for large-scale sample multiplexing, Nucleic Acids Research 35:e130, pp. 1-9.
Pearson W.R., et al., 1988, Improved tools for biological sequence comparison, PNAS 85(8):2444-8.
Pertea, et al., 2003, TIGR gene indices clustering tools (TGICL), Bioinformatics 19(5):651-52.
Pieles, et al., 1993, Matrix-assisted laser desorption ionization time-of-flight mass spectrometry: A powerful tool for the mass and sequence analysis of natural and modified oligonucleotides, Nucleic Acids Res 21:3191-3196.
Procter, et al., 2006, Molecular Diagnosis of Prader-Willi and Angelman Syndromes by Methylation-Specific Melting Analysis and Methylation-Specific Multiplex Ligation-Dependent Probe Amplification, Clinical Chemistry 52(7):1276-83.
Rambaut, et al., 1997, Seq-Gen:an application for the Monte Carlo simulation of DNA sequence evolution along phylogenetic trees, Bioinformatics (formerly CABIOS) 13:235-38.
Richter, et al., 2008, MetaSim—A Sequencing Simulator for Genomics and Metagenomics, PLOS ONE 3:e3373.
Rosendahl, et al., 2013, CFTR, SPINK1, CTRC and PRSS1 variants in chronic pancreatitis: is the role of mutated CFTR over estimated?, Gut 62:585-92.
Rothberg, et al., 2011, An integrated semiconductor device enablingnon-optical genome sequencing, Nature 475:348-52.
Rowntree, et al., 2003, The Phenotypic Consequences of CFTR Mutations, Annals of Human Genetics 67:471-85.
Sanger, et al., 1977, DNA sequencing with chain-terminating inhibitors, Proc.National Academy of Science USA 74(12):5463-7.
Santa Lucia, John Jr., 1998, A unified view of polymer, dumbbell, and oligonucleotide DNA nearest-neighbor thermodynamics, Proc. National Academy of Science USA 95:1460-5.
Sauro, 2004, How Do You Calculate a Z-Score/ Sigma Level?, https://www.measuringusability.com/zcalc.htm (online publication).
Sauro, 2004, What's a Z-Score and Why Use it in Usability Testing?, https://www.measuringusability.com/z.htm (online publication).
Schadt, et al., 2010, A window into third-generation sequencing, Human Molecular Genetics 19(R2):R227-40.
Schatz, et al., 2010, Assembly of large genomes using second-generation sequencing, Genome Res., 20:1165-1173.
Schrijver, et al., 2005, Diagnostic Testing by CFTR Gene Mutation Analysis in a Large Group of Hispanics, The Journal of Molecular Diagnostics 7:289-99.
Schuette, et al., 1995, Sequence analysis of phosphorothioate oligonucleotides via matrix-assisted laser desorption ionization time-of-flight mass spectrometry, J. Pharm. Biomed. Anal 13:1195-1203.
Schwartz, et al., 2009, Identification of Cystic Fibrosis Variants by Polymerase Chain Reaction/Oligonucleotide Ligation Assay, The Journal of Molecular Diagnostics 11(3):211-15.
Schwartz, Stuart, 2011, Clinical Utility of Single Nucleotide Polymorphism Arrays, Clinics in Laboratory Medicine 31(4):581-94.
Sequeira, et al., 1997, Implementing generic, object-oriented models in biology, Ecological Modeling 94.1:17-31.
Sievers F., et al., 2011, Fast, scalable generation of high-quality protein multiple sequence alignments using Clustal Omega, Mol Syst Biol 7:539.
Simpson, J.T., et al., 2009, ABySS: A parallel assembler for short read sequence data, Genome Res., 19(6): 1117-23.
Slater, G., & Birney, E, 2005, Automated generation of heuristics for biological sequence comparison, BMC Bioinformatics 6:31.
Spanu, P.D., et al., 2010, Genome expansion and gene loss in powdery mildew fungi reveal tradeoffs in extreme parasitism, Science 330(6010): 1543-46.

(56) References Cited

OTHER PUBLICATIONS

Summerer, Daniel, 2009, Enabling technologies of genomic-scale sequence enrichment for targeted high-throughput sequencing, Genomics 94:363-8.
Thauvin-Robinet, et al., 2009, The very low penetrance of cystic fibrosis for the R117H mutation: a reappraisal for genetic counselling and newborn screening, Journal of Medical Genetics 46:752-8.
Thompson, et al., 1994, CLUSTAL W: improving the sensitivity of progressive multiple sequence alignment through sequence weighting, position-specific gap penalities and matrix choice, Nucl. Acids. Res., 22:4673-80.
Thorvaldsdottir, et al., 2012, Integrative GenomicsViewer (IGV): high-performance genomics data visualization and exploration, Briefings in Bioinformatics 24(2):178-92.
Tokino, 1996, Characterization of the human p57 KIP2 gene: alternative splicing, insertion/deletion polymorphisms in VNTR sequences in the coding region, and mutational analysis, Human Genetics 96:625-31.
Turner, et al., 2009, Massively parallel exon capture and library-free resequencing acrossl6 genomes, nature methods 6:315-6 (and supplement).
Turner, et al., 2009, Methods for Genomic Partitioning, Annual Review of Genomics and Human Genetics 10:263-84.
Wallace, et al., 1979, Hybridization of synthetic oligodeoxyribonucteotides to dp x 174DNA:the effect of single base pair mismatch, Nucleic Acids Research 6:3543-3557.
Warner, et al. 1996, A general method for the detection of large CAG repeat expansions by fluorescent PCR, Journal Medical Genetics 33(12):1022-6.
Warren, R., et al., 2007, Assembling millions of short DNA sequences using SSAKE, Bioinformatics, 23:500-501.
Watson, et al., 2004, Cystic fibrosis population carrier screening: 2004 revision of American College of Medical Genetics mutation panel, Genetics in Medicine 6(5).
Ball et al. Targeted and genome-scale methylomics reveals gene body signatures in human cell lines. Nat Biotechnol. 2009; 27:361-8.
Barany, F. (1991) PCR Methods and Applications 1:5-16.
Barany, F. (1991) PNAS 88:189-193.
Bickle TA, Kruger DH (Jun. 1993), "Biology of DNA restriction", Microbiol. Rev. 57(2):434-50.
Boyer, H.W. (1971) "DNA restriction and modification mechanisms in bacteria". Annu. Rev. Microbiol. 25: 153-76.
Braasch, D.A. et al. (2001) Chem & Biol. 8(1):1-7.
Braslaysky, et al. (2003) PNAS (USA), 100: 3960-3964.
Brown et al. (1979), Methods Enzymol., 68:109.
Chan et al. (2011) Nucl. Acids Res. 39(1): 1-18.
Chirgwin et al. (1979), Biochemistry 18:5294-5299.
Deng et al. (2009) Nat Biotech 27:353-60.
C. P. Ordahl et al., Nucleic Acids Res., 1976, 3: 2985-2999.
I. G. G Gut and S. Beck, "A procedure for selective DNA alkylation and detection by mass spectrometry," 1995; Nucl. Acids Res. 23(8):1367-1373.
Hardenbol et al. (2005) Genome Res. 15:269-75.
Harris, T. D. et al. (2008) Science 320:106-109.
J. B. W. Hammond et al., Biochemistry, 1996, 240: 298-300.
K. A. Browne, (2002) "Metal ion-catalyzed nucleic Acid alkylation and fragmentation," J. Am. Chem. Soc. 124(27):7950-7962.
Krishnakumar et al. (2008) Proc Natl Acad Sci USA 105:9296-301.
Margulies, M. et al. (2005), Nature, 437:376-380.
Maxam and Gilbert, A new method for sequencing DNA, Proc. Natl. Acad. Sci. USA. 1977; 74(2):560-564.
Moudrianakis E. N. and Beer M., Proc Natl Acad Sci USA. Mar. 1965; 53:564-71.
Narang et al. (1979) Methods Enzymol., 68:90-98.
Nickerson et al. (1990) PNAS 87:8923-8927.
Nielsen, P.E. et al. (1999) Peptide Nucleic Acids, Protocols and Applications, Norfolk: Horizon Scientific Press, p. 1-19.
Nordhoff et al., (2003) Nucl. Acid. Res., 21(15):3347-57.
P. J. Oefner et al., Nucleic Acids Res., 1996, 24:3879-3889.
P. Sunnucks et al., Genetics, 1996, 144:747-756.
Porreca et al., 2007, Nat Methods 4:931-6.
Quail, et al. (Nov. 2010) DNA: Mechanical Breakage. In: eLS. John Wiley & Sons, Chichester. doi:10.1002/9780470015902.a0005333.pub2.
S. Gustincich et al., BioTechniques, 1991, 11: 298-302.
Sargent et al. (1988) Methods Enzymol., 152:432.
Soni G V and Meller A. (2007) Clin Chem 53: 1996-2001.
Turner E.H. et al., Nat Methods. Apr. 6, 2009:1-2.
Williams RJ (2003). "Restriction endonucleases: classification, properties, and applications". Mol. Biotechnol. 23 (3): 225-43.
Wittung, P. et al. (1997) Biochemistry 36:7973-7979.
Thorstenson et al., 1998, Genome Res., Cold Spring Harbor Laboratory Press, 8:848-855.
Yuan R (1981). "Structure and mechanism of multifunctional restriction endonucleases". Annu. Rev. Biochem. 50: 285-319.
S. M. Aljanabi and I. Martinez, Nucl. Acids Res., 1997, 25:4692-4693.
Roberts RJ (Jan. 1980), "Restriction and modification enzymes and their recognition sequences," Nucleic Acids Res., 8 (1): r63-r80.
Akhras, M.S., et al., 2007, Connector Inversion Probe Technology: A Powerful OnePrimer Multiplex DNA Amplification System for Numerous Scientific Applications PLOS ONE 2(9):e915.
Alazard, et al., 2002, Sequencing of production-scale synthetic oligonucleotides by enriching for coupling failures using matrix-assisted laser desorption/ ionization time-of-flight mass spectrometry, Analytical biochemistry 301:57-64.
Albert, 2007, Direct selection of human genomic loci by microarray hybridization, Nature Methods 4(11):903-5.
Antonarakis & the Nomenclature Working Group, 1998, Recommendations for a nomenclature system for human gene mutations, Human Mutation 11:1-3.
Bau, et al., 2008, Targeted next-generation sequencing by specific capture of multiple genomic loci using low-volume microfluidic DNA arrays, Analytical and bioanalytical chem 393(1):171-5.
Benner, et al., 2001, Evolution, language and analogy in functional genomics, Trends in Genetics 17:414-8.
Bentzley, et al., 1996, Oligonucleotide sequence and composition determined by matrix-assisted laser desorption/ ionization, Anal Chem 68:2141-2146.
Bentzley, et al., 1998, Base specificity of oligonucleotide digestion by calf spleen phosphodiesterase with matrixassisted laser desorption ionization analysis, Anal Biochem 258:31-37.
Bunyan, et al., 2004, Dosage analysis of cancer predisposition genes by multiplex ligation-dependent probe amplification, British Journal of Cancer, 91(6):1155-59.
Burrow & Wheeler, 1994, A block-sorting lossless data compression algorithm, Technical Report 124, Digital Equipment Corporation, CA.
Castellani, et al., 2008, Consensus on the use and interpretation of cystic fibrosis mutation analysis in clinical practice, Journal of Cystic Fibrosis 7(3):179-96.
Wu & Aboleneed, 2001, Improved oligonucleotide sequencing by alkaline phosphatase and exonuclease digestions with mass spectrometry, Anal Biochem 290:347-352.
Wu, et al., 1998, Sequencing regular and labeled oligonucleotides using enzymatic digestion and ionspray mass spectrometry, Anal Biochem 263:129-138.
Yau, et al., 1996, Accurate diagnosis of carriers of deletions and duplications in Duchenne/Becker muscular dystrophy by fluorescent dosage analysis, Journal Medical Genetics 33(7):550-8.
Yoo, et al., 2009, Applications of DNA Microarray in Disease Diagnostics, Journal of Microbiology and Biotechnology 19(7):635-46.
Yoshida, et al., 2004, Role of BRCA1 and BRCA2 as regulators of DNA repair, transcription, and cell cycle in response to DNA damage, Cancer Science 95(11)866-71.
Yu, 2007, A Novel Set of DNA Methylation Markers in Urine Sediments for Sensitive/Specific Detection of Bladder Cancer, Clinical Cancer Research 13(24):7296-7304.
Zerbino D.R., et al., 2008, Velvet: algorithms for de novo short read assembly using de Bruijn graphs, Genome Research 18 (5):821-829.
Zhang, et al., 2011, Is Mitochondrial tRNAphe Variant m.593T.Ca Synergistically Pathogenic Mutation in Chinese LHON Families with m.11778G.A? PLOS ONE 6(10):e26511.

(56) References Cited

OTHER PUBLICATIONS

Zhao F., et al., 2009, PGA4genomics for comparative genome assembly based on genetic algorithm optimization, Genomics. 94(4):284-6.

Zheng, et al. 2011, iAssembler: a package for de novo assembly of Roche-454/Sanger transcriptome sequences, BMC. Bioinformatics 12:453.

Zimmerman, et al., 2010, A novel custom resequencing array for dilated cardiomyopathy, Genetics in Medicine 12(5):268-78.

International Search Report and Written Opinion for WO2010/126614.

International Preliminary Report on Patentability for PCT/US2010/01293.

European Search Report for EP application No. 10770071.8, dated Nov. 8, 2012.

International Search Report and Written Opinion mailed on Oct. 28, 2010, for Patent Application No. PCT/US2010/001293, filed Apr. 30, 2010 (8 pages).

International Search Report and Written Opinion mailed Apr. 3, 2012, for International Patent Application No. PCT/US2011/065098, filed Dec. 15, 2011 (8 pages).

International Search Report and Written Opinion mailed Jun. 14, 2012, for International Patent Application No. PCT/US12/29790, filed Mar. 20, 2012 (8 pages).

Exam Report from EPO for EP 10770071.8, dated Jul. 16, 2013.

International Preliminary Report on Patentability for PCT/US2010/01293, dated Oct. 28, 2010.

International Search Report and Written Opinion mailed on Jun. 28, 2013, for Patent Application No. PCT/US2013/032885, filed Mar. 19, 2013 (9 pages).

International Search Report and Written Opinion mailed Jun. 10, 2013, for International Patent Application No. PCT/US13/33435, filed Mar. 22, 2013 (6 pages).

International Search Report and Written Opinion mailed Feb. 25, 2013 for International Patent Application No. PCT/US12/55362.

International Search Report and Written Opinion mailed Aug. 12, 2013, for International Patent Application No. PCT/US13/36575, filed Apr. 15, 2013 (9 pages).

International Search Report and Written Opinion mailed on Jun. 28, 2013, for Patent Application No. PCT/US2013/032885, filed Mar. 19, 2013 (6 pages).

International Search Report and Written Opinion mailed Nov. 1, 2013, for International Patent Application No. PCT/US2013/044039, filed Jun. 4, 2013 (6 pages).

International Search Report and Written Opinion mailed on Feb. 4, 2014, for Patent Application No. PCT/US13/62842, filed Oct. 1, 2013 (5 pages).

Alazard, et al., 2005, Sequencing Oligonucleotides by Enrichment of Coupling Failures Using Matrix-Assisted Laser Desorption/Ionization Time-of-Flight Mass Spectrometry, Current Protocols in Nucleic Acid Chemistry 10.10.1-10.10.7.

Browne, Kenneth A., 2002, Metal ion-catalyzed nucleic acid alkylation and fragmentation, Journal of American Chemical Society, 124(27)7950-62.

Thompson, et al., 2011, The properties and applications of single-molecule DNA sequencing, Genome Biology 12(2):217, 10 pages.

Australian Patent Examination Report No. 1 issued Aug. 12, 2014, for Australian Patent Application No. 2010242073 filed Apr. 30, 2010, 4 pages.

Supplementary European Search Report issued Aug. 26, 2014, for European Patent Application No. 12765217.0, filed Mar. 20, 2012, 5 pages.

International Search Report and Written Opinion mailed on Sep. 3, 2014 for International Patent Application No. PCT/US14/27324, filed Mar. 14, 2014 (7 pages).

\* cited by examiner

METHODS FOR ANALYZING NUCLEIC ACIDS

RELATED APPLICATION

The present application is a continuation of U.S. nonprovisional application Ser. No. 14/210,776, filed Mar. 14, 2014, which claims the benefit of and priority to U.S. provisional patent application Ser. No. 61/784,624, filed Mar. 14, 2013, the content of each of which is incorporated by reference herein in its entirety.

FIELD OF THE INVENTION

The invention generally relates to methods for analyzing nucleic acids.

BACKGROUND

Information about the genotype of a subject is becoming more important and relevant for a range of healthcare decisions as the genetic basis for many diseases, disorders, and physiological characteristics is further elucidated. Medical advice is increasingly personalized, with individual decisions and recommendations being based on specific genetic information.

For cost-effective and reliable medical and reproductive counseling on a large scale, it is important to be able to correctly and unambiguously identify the allelic status for many different genetic loci in many subjects. Numerous technologies have been developed for detecting and analyzing nucleic acid sequences from biological samples. A commonly used analysis technology is sequencing. Massively parallel DNA sequencing technologies have greatly increased the ability to generate large amounts of sequencing data at a rapid pace.

As sequencing has increased the ability to probe many genomic loci at once, molecular protocols have been developed to selectively enrich for loci of interest. One such protocol uses molecular inversion probes. A molecular inversion probe is composed of a common linker sequence and two unique targeting arms that hybridize to genomic regions flanking a target. In a capture protocol, probes are tiled across a region of a nucleic acid template to ensure overlapping coverage. The hybridized probes are then filled-in with polymerase and the circularized probe is closed with ligase. Following circularization of the probes, the remaining linear (un-captured) genomic DNA is digested away with exonuclease (leaving only the captured targets within the circularized probes). The probes are then sequenced and sequence data is assembled together. That assembled sequence is analyzed for mutations.

A problem with tiling is that multiple probes contain a portion of the same sequence on the same nucleic acid strand, and therefore compete with each other to bind the same region on the same strand. That competition results in fewer capture events per targeted genomic region and thus decreases capture efficiency.

SUMMARY

The invention solves problems associated with tiling by providing molecular inversion probes that are designed such that immediately adjacent probes hybridize to opposite strands of a nucleic acid template and probes on the same strand hybridize to the template in an overlapping manner. In that manner, when probes of the invention are used for tiling, immediately adjacent probes do not compete with each other to bind the same genomic region of the template, and probes still provide overlapping coverage of the template. Accordingly, methods of the invention ensure that there is less competition between probes for a target region of a nucleic acid template, resulting in more capture events per targeted genomic region and increased capture efficiency.

Aspects of the invention involve obtaining a sample including a nucleic acid template. A plurality of molecular inversion probes are tiled across a portion of the template. The probes are designed such that immediately adjacent probes hybridize to opposite strands of the nucleic acid template and probes on the same strand hybridize to the template in an overlapping manner. A region between targeting arms of a plurality of the molecular inversion probes is filled-in with nucleotides, and the filled-in region of a plurality of the probes is analyzed to obtain sequence information about the nucleic acid template. The region between the arms may be filled with a ligase, a polymerase, or a combination thereof. Generally, a polymerase is used to fill the region, and a ligase is used to close each circularized probe.

Any method known in the art may be used to analyze the probes. A particularly useful method is sequencing, such as sequencing-by-synthesis and single molecule sequencing-by-synthesis. However, any sequencing platform may be used with methods of the invention. Alternatively, probe hybridization, PCR, or real-time PCR can be used to analyze the probes. In some embodiments, the probes are amplified prior to sequencing. In other embodiments, the probes are sequenced without prior amplification.

If sequencing is used as the analysis method, then the probes can undergo a standard sequencing workflow prior to being sequenced. Such workflow may involve attaching barcodes and/or sequencing adaptors to the probes prior to sequencing. The probes may or may not be attached to a solid support for sequencing. Exemplary solid supports are flow cells, beads, or any planar substrate.

The analysis method is used to look for mutations in the sequence information, such as a single nucleotide polymorphism (SNP), an insertion, a deletion, an inversion, a translocation, a substitution, or any combination thereof.

DETAILED DESCRIPTION

Figure 1:
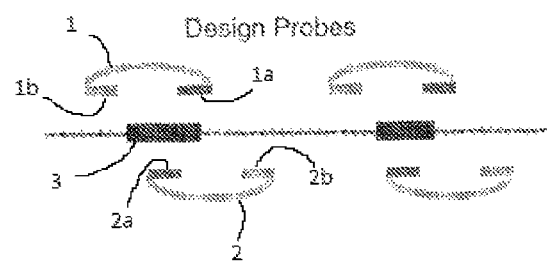
FIG. 1 is a schematic illustrating immediately adjacent molecular inversion probes hybridizing to opposite strands of a nucleic acid template.

The invention generally relates to methods for analyzing nucleic acids. In certain aspects, methods of the invention involve obtaining a sample including a nucleic acid template. A plurality of molecular inversion probes are tiled across a portion of the template. The probes are designed such that immediately adjacent probes hybridize to opposite strands of the nucleic acid template and probes on the same strand hybridize to the template in an overlapping manner. A region between targeting arms of a plurality of the molecular inversion probes is filled-in with nucleotides, and the filled-in region of a plurality of the probes is analyzed to obtain sequence information about the nucleic acid template.

Samples

In certain aspects, methods of the invention involve obtaining a sample. The sample is typically a tissue or body fluid that is obtained in any clinically acceptable manner. A tissue is a mass of connected cells and/or extracellular matrix material, e.g. skin tissue, endometrial tissue, nasal passage tissue, CNS tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed.

Nucleic acid is extracted from the sample according to methods known in the art. See for example, Maniatis, et al., Molecular Cloning: A Laboratory Manual, Cold Spring Harbor, N.Y., pp. 280-281, 1982, the contents of which are incorporated by reference herein in their entirety. See also techniques described in Sambrook, J., Fritsch, E. F., and Maniatis, T. (1989) Molecular Cloning: A Laboratory Manual, 2nd ed. Cold Spring Harbor, N.Y.: Cold Spring Harbor Laboratory.), the contents of which are incorporated by reference herein. Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). Several protocols have been developed to extract genomic DNA from blood.

There are also numerous kits that can be used to extract DNA from tissues and bodily fluids and that are commercially available from, for example, BD Biosciences Clontech (Palo Alto, Calif.), Epicentre Technologies (Madison, Wis.), Gentra Systems, Inc. (Minneapolis, Minn.), MicroProbe Corp. (Bothell, Wash.), Organon Teknika (Durham, N.C.), Qiagen Inc. (Valencia, Calif.), Autogen (Holliston, Mass.); Beckman Coulter (Brea, Calif.), (AutoGenFlex STAR robot with Qiagen FlexiGene chemistry. For example, Autogen manufactures FlexStar automated extraction kits used in combination with Qiagen FlexiGene Chemistry, and Beckman Coulter manufactures Agencourt GenFind kits for bead-based extraction chemistry. User Guides that describe in detail the protocol(s) to be followed are usually included in all these kits, for example, Qiagen's literature for their PureGene extraction chemistry entitled "Qiagen PureGene Handbook" 3rd Edition, dated June 2011.

In certain embodiments, a genomic sample is collected from a subject followed by enrichment for genes or gene fragments of interest, for example by hybridization to a nucleotide array. The sample may be enriched for genes of interest using methods known in the art, such as hybrid capture. See for examples, Lapidus (U.S. Pat. No. 7,666,593), the content of which is incorporated by reference herein in its entirety. As will be described in more detail below, a preferable capture method uses molecular inversion probes.

RNA may be isolated from eukaryotic cells by procedures that involve lysis of the cells and denaturation of the proteins contained therein. Tissue of interest includes liver cells. RNA may be isolated from fluids of interest by procedures that involve denaturation of the proteins contained therein. Fluids of interest include blood. Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., Biochemistry 18:5294-5299 (1979)). Poly (A)+RNA is selected by selection with oligo-dT cellulose (see Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol. If desired, RNase inhibitors may be added to the lysis buffer. Likewise, for certain cell types, it may be desirable to add a protein denaturation/digestion step to the protocol.

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or SEPHADEX (see Ausubel et al., CURRENT PROTOCOLS IN MOLECULAR BIOLOGY, vol. 2, Current Protocols Publishing, New York (1994). Once bound, poly (A)+mRNA is eluted from the affinity column using 2 mM EDTA/0.1% SDS.

Fragmenting the Nucleic Acid

Nucleic acids, including genomic nucleic acids, can be fragmented using any of a variety of methods, such as mechanical fragmenting, chemical fragmenting, and enzymatic fragmenting. Methods of nucleic acid fragmentation are known in the art and include, but are not limited to, DNase digestion, sonication, mechanical shearing, and the like (J. Sambrook et al., "Molecular Cloning: A Laboratory Manual", 1989, 2.sup.nd Ed., Cold Spring Harbour Laboratory Press: New York, N.Y.; P. Tijssen, "Hybridization with Nucleic Acid Probes—Laboratory Techniques in Biochemistry and Molecular Biology (Parts I and II)", 1993, Elsevier; C. P. Ordahl et al., Nucleic Acids Res., 1976, 3: 2985-2999; P. J. Oefner et al., Nucleic Acids Res., 1996, 24: 3879-3889; Y. R. Thorstenson et al., Genome Res., 1998, 8: 848-855). U.S. Patent Publication 2005/0112590 provides a general overview of various methods of fragmenting known in the art.

Genomic nucleic acids can be fragmented into uniform fragments or randomly fragmented. In certain aspects, nucleic acids are fragmented to form fragments having a fragment length of about 5 kilobases or 100 kilobases. In a preferred embodiment, the genomic nucleic acid fragments can range from 1 kilobases to 20 kilobases. Preferred fragments can vary in size and have an average fragment length of about 10 kilobases. However, desired fragment length and ranges of fragment lengths can be adjusted depending on the type of nucleic acid targets one seeks to capture and the design and type of molecular inversion probes. The particular method of fragmenting is selected to achieve the desired fragment length. A few non-limiting examples are provided below.

Chemical fragmentation of genomic nucleic acids can be achieved using a number of different methods. For example, hydrolysis reactions including base and acid hydrolysis are common techniques used to fragment nucleic acid. Hydrolysis is facilitated by temperature increases, depending upon the desired extent of hydrolysis. Fragmentation can be accomplished by altering temperature and pH as described below. The benefit of pH-based hydrolysis for shearing is that it can result in single-stranded products. Additionally, temperature can be used with certain buffer systems (e.g. Tris) to temporarily shift the pH up or down from neutral to accomplish the hydrolysis, then back to neutral for long-term storage etc. Both pH and temperature can be modulated to effect differing amounts of shearing (and therefore varying length distributions).

Other methods of hydrolytic fragmenting of nucleic acids include alkaline hydrolysis, formalin fixation, hydrolysis by metal complexes (e.g., porphyrins), and/or hydrolysis by hydroxyl radicals. RNA shears under alkaline conditions, see, e.g. Nordhoff et al., Nucl. Acid. Res., 21 (15):3347-57 (2003), whereas DNA can be sheared in the presence of strong acids.

An exemplary acid/base hydrolysis protocol for producing genomic nucleic acid fragments is described in Sargent et al. (1988) Methods Enzymol., 152:432. Briefly, 1 g of purified DNA is dissolved in 50 mL 0.1 N NaOH. 1.5 mL concentrated HCl is added, and the solution is mixed quickly. DNA will precipitate immediately, and should not be stirred for more than a few seconds to prevent formation of a large aggregate. The sample is incubated at room temperature for 20 minutes to partially depurinate the DNA. Subsequently, 2 mL 10 N NaOH (OH—concentration to 0.1 N) is added, and the sample is stirred until the DNA redissolves completely. The sample is then incubated at 65 degrees C. for 30 minutes in order to hydrolyze the DNA. Resulting fragments typically range from about 250-1000 nucleotides but can vary lower or higher depending on the conditions of hydrolysis.

In one embodiment, after genomic nucleic acid has been purified, it is resuspended in a Tris-based buffer at a pH between 7.5 and 8.0, such as Qiagen's DNA hydrating solution. The resuspended genomic nucleic acid is then heated to 65° C. and incubated overnight. Heating shifts the pH of the buffer into the low- to mid-6 range, which leads to acid hydrolysis. Over time, the acid hydrolysis causes the genomic nucleic acid to fragment into single-stranded and/or double-stranded products.

Chemical cleavage can also be specific. For example, selected nucleic acid molecules can be cleaved via alkylation, particularly phosphorothioate-modified nucleic acid molecules (see, e.g., K. A. Browne, "Metal ion-catalyzed nucleic Acid alkylation and fragmentation," J. Am. Chem. Soc. 124 (27):7950-7962 (2002)). Alkylation at the phosphorothioate modification renders the nucleic acid molecule susceptible to cleavage at the modification site. See I. G. Gut and S. Beck, "A procedure for selective DNA alkylation and detection by mass spectrometry," Nucl. Acids Res. 23(8):1367-1373 (1995).

Methods of the invention also contemplate chemically shearing nucleic acids using the technique disclosed in Maxam-Gilbert Sequencing Method (Chemical or Cleavage Method), Proc. Natl. Acad. Sci. USA. 74:560-564. In that protocol, the genomic nucleic acid can be chemically cleaved by exposure to chemicals designed to fragment the nucleic acid at specific bases, such as preferential cleaving at guanine, at adenine, at cytosine and thymine, and at cytosine alone.

Mechanical shearing of nucleic acids into fragments can occur using any method known in the art. For example, fragmenting nucleic acids can be accomplished by hydroshearing, trituration through a needle, and sonication. See, for example, Quail, et al. (November 2010) DNA: Mechanical Breakage. In: eLS. John Wiley & Sons, Chichester. doi: 10.1002/9780470015902.a0005 333.pub2.

The nucleic acid can also be sheared via nebulization, see (Roe, B A, Crabtree. J S and Khan, A S 1996); Sambrook & Russell, Cold Spring Harb Protoc 2006. Nebulizing involves collecting fragmented DNA from a mist created by forcing a nucleic acid solution through a small hole in a nebulizer. The size of the fragments obtained by nebulization is determined chiefly by the speed at which the DNA solution passes through the hole, altering the pressure of the gas blowing through the nebulizer, the viscosity of the solution, and the temperature. The resulting DNA fragments are distributed over a narrow range of sizes (700-1330 bp). Shearing of nucleic acids can be accomplished by passing obtained nucleic acids through the narrow capillary or orifice (Oefner et al., Nucleic Acids Res. 1996; Thorstenson et al., Genome Res. 1995). This technique is based on point-sink hydrodynamics that result when a nucleic acid sample is forced through a small hole by a syringe pump.

In HydroShearing (Genomic Solutions, Ann Arbor, Mich., USA), DNA in solution is passed through a tube with an abrupt contraction. As it approaches the contraction, the fluid accelerates to maintain the volumetric flow rate through the smaller area of the contraction. During this acceleration, drag forces stretch the DNA until it snaps. The DNA fragments until the pieces are too short for the shearing forces to break the chemical bonds. The flow rate of the fluid and the size of the contraction determine the final DNA fragment sizes.

Sonication is also used to fragment nucleic acids by subjecting the nucleic acid to brief periods of sonication, i.e. ultrasound energy. A method of shearing nucleic acids into fragments by sonification is described in U.S. Patent Publication 2009/0233814. In the method, a purified nucleic acid is obtained placed in a suspension having particles disposed within. The suspension of the sample and the particles are then sonicated into nucleic acid fragments.

An acoustic-based system that can be used to fragment DNA is described in U.S. Pat. Nos. 6,719,449, and 6,948,843 manufactured by Covaris Inc. U.S. Pat. No. 6,235,501 describes a mechanical focusing acoustic sonication method of producing high molecular weight DNA fragments by application of rapidly oscillating reciprocal mechanical energy in the presence of a liquid medium in a closed container, which may be used to mechanically fragment the DNA.

Another method of shearing nucleic acids into fragments uses ultrasound energy to produce gaseous cavitation in liquids, such as shearing with Diagonnode's BioRuptor®. Cavitation is the formation of small bubbles of dissolved gases or vapors due to the alteration of pressure in liquids. These bubbles are capable of resonance vibration and produce vigorous eddying or microstreaming. The resulting mechanical stress can lead to shearing the nucleic acid in to fragments.

Enzymatic fragmenting, also known as enzymatic cleavage, cuts nucleic acids into fragments using enzymes, such as endonucleases, exonucleases, ribozymes, and DNAzymes. Such enzymes are widely known and are available commercially, see Sambrook, J. Molecular Cloning: A Laboratory Manual, 3rd (2001) and Roberts R J (January 1980). "Restriction and modification enzymes and their recognition sequences," Nucleic Acids Res. 8 (1): r63-r80. Varying enzymatic fragmenting techniques are well-known in the art, and such techniques are frequently used to fragment a nucleic acid for sequencing, for example, Alazard et al, 2002; Bentzley et al, 1998; Bentzley et al, 1996; Faulstich et al, 1997; Glover et al, 1995; Kirpekar et al, 1994; Owens et al, 1998; Pieles et al, 1993; Schuette et al, 1995; Smirnov et al, 1996; Wu & Aboleneen, 2001; Wu et al, 1998a.

The most common enzymes used to fragment nucleic acids are endonucleases. The endonucleases can be specific for either a double-stranded or a single stranded nucleic acid molecule. The cleavage of the nucleic acid molecule can occur randomly within the nucleic acid molecule or can cleave at specific sequences of the nucleic acid molecule. Specific fragmentation of the nucleic acid molecule can be accomplished using one or more enzymes in sequential reactions or contemporaneously.

Restriction endonucleases recognize specific sequences within double-stranded nucleic acids and generally cleave both strands either within or close to the recognition site in order to fragment the nucleic acid. Naturally occurring restriction endonucleases are categorized into four groups (Types I, II III, and IV) based on their composition and enzyme cofactor requirements, the nature of their target sequence, and the position of their DNA cleavage site relative to the target sequence. Bickle T A, Kruger D H (June 1993). "Biology of DNA restriction". Microbiol. Rev. 57 (2): 434-50; Boyer H W (1971). "DNA restriction and modification mechanisms in bacteria". Annu. Rev. Microbiol. 25: 153-76; Yuan R (1981). "Structure and mechanism of multifunctional restriction endonucleases". Annu. Rev. Biochem. 50: 285-319. All types of enzymes recognize specific short DNA sequences and carry out the endonucleolytic cleavage of DNA to give specific fragments with terminal 5'-phosphates. The enzymes differ in their recognition sequence, subunit composition, cleavage position, and cofactor requirements. Williams R J (2003). "Restriction endonucleases: classification, properties, and applications". Mol. Biotechnol. 23 (3): 225-43.

Where restriction endonucleases recognize specific sequencings in double-stranded nucleic acids and generally cleave both strands, nicking endonucleases are capable of cleaving only one of the strands of the nucleic acid into a fragment. Nicking enzymes used to fragment nucleic acids can be naturally occurring or genetically engineered from restriction enzymes. See Chan et al., Nucl. Acids Res. (2011) 39 (1): 1-18.

Capture and Tiling of Target Sequences

Any method known in the art for capturing target sequences may be used with methods of the invention. In certain embodiments, molecular inversion probes (MIP) are used with methods of the invention and an oligonucleotide-driven annealing reaction is performed between genomic DNA and target-specific probes to form open loop complexes, where the target sequence is flanked by the ends of each oligo. Then, polymerase and ligase enzymes are added to fill and seal the gap between the two oligonucleotide probe ends, forming a covalently-closed circular molecule that contains the target sequence. Finally, an exonuclease mix is added to degrade any non-circular DNA (un-reacted probe, genomic DNA). What remains is circular DNA containing the set of targets captured by the reaction. Further details are provided for example in the following U.S. Pat. Nos. 5,866, 337; 7,790,388; 6,858,412; 7,993,880; 7,700,323; 6,558,928; 6,235,472; 7,320,860; 7,351,528; 7,074,564; 5,871,921; 7,510,829; 7,862,999; and 7,883,849, the content of each of which is incorporated by reference herein in its entirety. Particular molecular inversion probes that are useful with methods of the invention are described in Porreca et al. (U.S. patent application Ser. No. 13/934,093), the content of which is incorporated by reference herein in its entirety. Molecular inversion probes and methods for using such probes are further described, for example in Porreca et al. (International patent application publication number WO 2010/126614), the content of which is incorporated by reference herein in its entirety.

Molecular inversion probe technology is used to detect or amplify particular nucleic acid sequences in complex mixtures. Use of molecular inversion probes has been demonstrated for detection of single nucleotide polymorphisms (Hardenbol et al. 2005 Genome Res 15:269-75) and for preparative amplification of large sets of exons (Porreca et al. 2007 Nat Methods 4:931-6, Krishnakumar et al. 2008 Proc Natl Acad Sci USA 105:9296-301). One of the main benefits of the method is in its capacity for a high degree of multiplexing, because generally thousands of targets may be captured in a single reaction containing thousands of probes.

In certain embodiments, molecular inversion probes include a universal portion flanked by two unique targeting arms. The targeting arms are designed to hybridize immediately upstream and downstream of a specific target sequence located on a genomic nucleic acid template. The molecular inversion probes are introduced to nucleic acid to perform capture of target sequences located on the template. According to the invention, the probes are designed such that immediately adjacent probes hybridize to opposite strands of a nucleic acid template. Probes are immediately adjacent when they hybridize to a nucleic acid template in a manner in which a first targeting arm of a first probe and a first targeting arm of a second probe hybridize to a target without a targeting arm of a third probe hybridizing between the first targeting arm of the first probe and the first targeting arm of the second probe. That is illustrated in FIG. 1, which shows a first molecular inversion probe 1 and a second molecular inversion probe 2. Both probes are hybridized to a region 3 of the template. Probe 1 has a targeting arm 1a and a targeting arm 1b. Probe 2 has a targeting arm 2a and a targeting arm 2b. The probes hybridize to region 3 of the template such that probe 1 hybridizes to a first strand of the region 3 and probe 2 hybridizes to a second strand of region 3. The probes 1 and 2 are configured such that they hybridize to the region 3 in a manner in which targeting arm 1a of probe 1 is immediately adjacent to targeting arm 2a of probe 2. That is, probes 1 and 2 hybridize to region 3 in a manner in which targeting arm 1a of probe 1 and targeting arm 2a of probe 2 hybridize to region 3 without a targeting arm of a third probe being able to hybridize between targeting arm 1a of the probe 1 and targeting arm 2a of probe 2. Immediately adjacent probes can hybridize such that the targeting arms abut each other, as shown in FIG. 1. However, immediately adjacent probes do not need to hybridize such that they abut each other, and immediately adjacent probes can hybridize such that they are spaced apart from each other on the template. Due to immediately adjacent molecular inversion probes hybridizing to opposite strands, there is less competition between probes for a target region of a nucleic acid template, resulting in more capture events per targeted genomic region and increased capture efficiency.

After capture of the target sequence of interest, the captured target may further be subjected to an enzymatic gap-filling and ligation step, such that a copy of the target sequence is incorporated into a circle. Capture efficiency of the MIP to the target sequence on the nucleic acid fragment can be improved by lengthening the hybridization and gap-filing incubation periods. (See, e.g., Turner E H, et al., Nat Methods. 2009 April 6:1-2.).

The result of MIP capture as described above is a library of circular target probes, which then can be processed in a variety of ways. In one aspect, adaptors for sequencing can be attached during common linker-mediated PCR, resulting in a library with non-random, fixed starting points for sequencing.

In another aspect, for preparation of a shotgun library, a common linker-mediated PCR is performed on the circle target probes, and the post-capture amplicons are linearly concatenated, sheared, and attached to adaptors for sequencing. Methods for shearing the linear concatenated captured targets can include any of the methods disclosed for fragmenting nucleic acids discussed above. In certain aspects, performing a hydrolysis reaction on the captured amplicons in the presence of heat is the desired method of shearing for library production.

Accordingly, it should be appreciated that in any of the embodiments for molecular inversion probes capture described herein (e.g., tiling/staggering), involve contacting fragmented genomic nucleic acid(s) with one or more different molecular inversion probes. In some embodiments, the amount of genomic nucleic acid used per subject ranges from 1 ng to 10 micrograms (e.g., 500 ng to 5 micrograms). However, higher or lower amounts (e.g., less than 1 ng, more than 10 micrograms, 10-50 micrograms, 50-100 micrograms or more) may be used. In some embodiments, for each locus of interest, the amount of probe used per assay may be optimized for a particular application. In some embodiments, the ratio (molar ratio, for example measured as a concentration ratio) of probe to genome equivalent (e.g., haploid or diploid genome equivalent, for example for each allele or for both alleles of a nucleic acid target or locus of interest) ranges from 1/100, 1/10, 1/1, 10/1, 100/1, 1000/1. However, lower, higher, or intermediate ratios may be used.

In some embodiments, the amount of target nucleic acid and probe used for each reaction is normalized to avoid any observed differences being caused by differences in concentrations or ratios. In some embodiments, in order to normalize genomic DNA and probe, the genomic DNA concentration is read using a standard spectrophotometer or by fluorescence (e.g., using a fluorescent intercalating dye). The probe concentration may be determined experimentally or using information specified by the probe manufacturer.

Similarly, once a locus has been captured, it may be amplified and/or sequenced in a reaction involving one or more primers. The amount of primer added for each reaction can range from 0.1 pmol to 1 nmol, 0.15 pmol to 1.5 nmol (for example around 1.5 pmol). However, other amounts (e.g., lower, higher, or intermediate amounts) may be used.

In some embodiments, it should be appreciated that one or more intervening sequences (e.g., sequence between the first and second targeting arms on a MIP capture probe), identifier or tag sequences, or other probe sequences that are not designed to hybridize to a target sequence (e.g., a genomic target sequence) should be designed to avoid excessive complementarity (to avoid cross-hybridization) to target sequences or other sequences (e.g., other genomic sequences) that may be in a biological sample. For example, these sequences may be designed to have a sufficient number of mismatches with any genomic sequence (e.g., at least 5, 10, 15, or more mismatches out of 30 bases) or to have a Tm (e.g., a mismatch Tm) that is lower (e.g., at least 5, 10, 15, 20, or more degrees C. lower) than the hybridization reaction temperature.

It should be appreciated that a targeting arm as used herein may be designed to hybridize (e.g., be complementary) to either strand of a genetic locus of interest if the nucleic acid being analyzed is DNA (e.g., genomic DNA). However, in the context of MIP probes, whichever strand is selected for one targeting arm will be used for the other one. However, in the context of RNA analysis, it should be appreciated that a targeting arm should be designed to hybridize to the transcribed RNA. It also should be appreciated that MIP probes referred to herein as "capturing" a target sequence are actually capturing it by template-based synthesis rather than by capturing the actual target molecule (other than for example in the initial stage when the arms hybridize to it or in the sense that the target molecule can remain bound to the extended MIP product until it is denatured or otherwise removed).

It should be appreciated that in some embodiments a targeting arm may include a sequence that is complementary to one allele or mutation (e.g., a SNP or other polymorphism, a mutation, etc.) so that the probe will preferentially hybridize (and capture) target nucleic acids having that allele or mutation. However, in many embodiments, each targeting arm is designed to hybridize (e.g., be complementary) to a sequence that is not polymorphic in the subjects of a population that is being evaluated. This allows target sequences to be captured and/or sequenced for all alleles and then the differences between subjects (e.g., calls of heterozygous or homozygous for one or more loci) can be based on the sequence information and/or the frequency as described herein.

It should be appreciated that sequence tags (also referred to as barcodes) may be designed to be unique in that they do not appear at other positions within a probe or a family of probes and they also do not appear within the sequences being targeted. Thus they can be used to uniquely identify (e.g., by sequencing or hybridization properties) particular probes having other characteristics (e.g., for particular subjects and/or for particular loci).

It also should be appreciated that in some embodiments probes or regions of probes or other nucleic acids are described herein as comprising or including certain sequences or sequence characteristics (e.g., length, other properties, etc.). In addition, components (e.g., arms, central regions, tags, primer sites, etc., or any combination thereof) of such probes can include certain sequences or sequence characteristics that consist of one or more characteristics (e.g., length or other properties, etc.).

It should be appreciated that probes, primers, and other nucleic acids designed or used herein may be synthetic, natural, or a combination thereof. Accordingly, as used herein, the term "nucleic acid" refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). "Nucleic acid" and "nucleic acid molecule" may be used interchangeably and refer to oligoribonucleotides as well as oligodeoxyribonucleotides. The terms shall also include polynucleosides (i.e., a polynucleotide minus a phosphate) and any other organic base containing nucleic acid.

The organic bases include adenine, uracil, guanine, thymine, cytosine and inosine. Unless otherwise stated, nucleic acids may be single or double stranded. The nucleic acid may be naturally or non-naturally occurring. Nucleic acids can be obtained from natural sources, or can be synthesized using a nucleic acid synthesizer (i.e., synthetic).

Harvest and isolation of nucleic acids are routinely performed in the art and suitable methods can be found in standard molecular biology textbooks. (See, for example, Maniatis' Handbook of Molecular Biology.) The nucleic acid may be DNA or RNA, such as genomic DNA, mitochondrial DNA, mRNA, cDNA, rRNA, miRNA, or a combination thereof. Non-naturally occurring nucleic acids such as bacterial artificial chromosomes (BACs) and yeast artificial chromosomes (YACs) can also be used.

The invention also contemplates the use of nucleic acid derivatives. As will be described herein, the use of certain nucleic acid derivatives may increase the stability of the nucleic acids of the invention by preventing their digestion, particularly when they are exposed to biological samples that may contain nucleases. As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages.

Nucleic acid derivatives may contain backbone modifications such as but not limited to phosphorothioate linkages, phosphodiester modified nucleic acids, phosphorothiolate modifications, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous.

Nucleic acid derivatives may contain substitutions or modifications in the sugars and/or bases. For example, they may include nucleic acids having backbone sugars which are covalently attached to low molecular weight organic groups other than a hydroxyl group at the 3' position and other than a phosphate group at the 5' position (e.g., an 2'-O-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine. In some embodiments, substitution(s) may include one or more substitutions/modifications in the sugars/bases, groups attached to the base, including biotin, fluorescent groups (fluorescein, cyanine, rhodamine, etc), chemically-reactive groups including carboxyl, NHS, thiol, etc., or any combination thereof.

A nucleic acid may be a peptide nucleic acid (PNA), locked nucleic acid (LNA), DNA, RNA, or co-nucleic acids of the same such as DNA-LNA co-nucleic acids. PNA are DNA analogs having their phosphate backbone replaced with 2-aminoethyl glycine residues linked to nucleotide bases through glycine amino nitrogen and methylenecarbonyl linkers. PNA can bind to both DNA and RNA targets by Watson-Crick base pairing, and in so doing form stronger hybrids than would be possible with DNA or RNA based oligonucleotides in some cases.

PNA are synthesized from monomers connected by a peptide bond (Nielsen, P. E. et al. Peptide Nucleic Acids, Protocols and Applications, Norfolk: Horizon Scientific Press, p. 1-19 (1999)). They can be built with standard solid phase peptide synthesis technology. PNA chemistry and synthesis allows for inclusion of amino acids and polypeptide sequences in the PNA design. For example, lysine residues can be used to introduce positive charges in the PNA backbone. All chemical approaches available for the modifications of amino acid side chains are directly applicable to PNA. Several types of PNA designs exist, and these include single strand PNA (ssPNA), bisPNA and pseudocomplementary PNA (pcPNA).

The structure of PNA/DNA complex depends on the particular PNA and its sequence. ssPNA binds to single stranded DNA (ssDNA) preferably in antiparallel orientation (i.e., with the N-terminus of the ssPNA aligned with the 3' terminus of the ssDNA) and with a Watson-Crick pairing. PNA also can bind to DNA with a Hoogsteen base pairing, and thereby forms triplexes with double stranded DNA (dsDNA) (Wittung, P. et al., Biochemistry 36:7973 (1997)).

A locked nucleic acid (LNA) is a modified RNA nucleotide. An LNA form hybrids with DNA, which are at least as stable as PNA/DNA hybrids (Braasch, D. A. et al., Chem & Biol. 8(1):1-7(2001)). Therefore, LNA can be used just as PNA molecules would be. LNA binding efficiency can be increased in some embodiments by adding positive charges to it. LNAs have been reported to have increased binding affinity inherently.

Commercial nucleic acid synthesizers and standard phosphoramidite chemistry are used to make LNAs. Therefore, production of mixed LNA/DNA sequences is as simple as that of mixed PNA/peptide sequences. The stabilization effect of LNA monomers is not an additive effect. The monomer influences conformation of sugar rings of neighboring deoxynucleotides shifting them to more stable configurations (Nielsen, P. E. et al. Peptide Nucleic Acids, Protocols and Applications, Norfolk: Horizon Scientific Press, p. 1-19 (1999)). Also, lesser number of LNA residues in the sequence dramatically improves accuracy of the synthesis. Most of biochemical approaches for nucleic acid conjugations are applicable to LNA/DNA constructs.

While probes have been typically designed to meet certain constraints (e.g. melting temperature, G/C content, etc.) known to partially affect capture/amplification efficiency (Ball et al (2009) Nat Biotech 27:361-8 AND Deng et al (2009) Nat Biotech 27:353-60), a set of constraints which is sufficient to ensure either largely uniform or highly reproducible capture/amplification efficiency has not previously been achieved.

As disclosed herein, uniformity and reproducibility can be increased by designing multiple probes per target, such that each base in the target is captured by more than one probe. In some embodiments, the disclosure provides multiple MIPs per target to be captured, where each MIP in a set designed for a given target nucleic acid has a central region and a 5' region and 3' region ('targeting arms') which hybridize to (at least partially) different nucleic acids in the target nucleic acid (immediately flanking a subregion of the target nucleic acid). Thus, differences in efficiency between different targeting arms and fill-in sequences may be averaged across multiple MIPs for a single target, which results in more uniform and reproducible capture efficiency.

In some embodiments, the methods involve designing a single probe for each target (a target can be as small as a single base or as large as a kilobase or more of contiguous sequence).

It may be preferable, in some cases, to design probes to capture molecules (e.g., target nucleic acids or subregions thereof) having lengths in the range of 1-200 bp (as used herein, a by refers to a base pair on a double-stranded nucleic acid—however, where lengths are indicated in bps, it should be appreciated that single-stranded nucleic acids having the same number of bases, as opposed to base pairs, in length also are contemplated by the invention). However, probe design is not so limited. For example, probes can be designed to capture targets having lengths in the range of up to 10, 20, 30, 40, 50, 60, 70, 80, 90, 100, 200, 300, 400, 500, 1000, or more bps, in some cases.

It is to be appreciated that the length of a capture molecule on a nucleic acid fragment (e.g., a target nucleic acid or subregion thereof) is selected based upon multiple considerations. For example, where analysis of a target involves sequencing, e.g., with a next-generation sequencer, the target length should typically match the sequencing read-length so that shotgun library construction is not necessary. However, it should be appreciated that captured nucleic acids may be sequenced using any suitable sequencing technique as aspects of the invention are not limited in this respect.

It is also to be appreciated that some target nucleic acids on a nucleic acid fragment are too large to be captured with one probe. Consequently, it may be necessary to capture multiple subregions of a target nucleic acid in order to analyze the full target.

In some embodiments, a sub-region of a target nucleic acid is at least 1 bp. In other embodiments, a subregion of a target nucleic acid is at least 10, 20, 30, 40, 50, 60, 70, 80, 90, 100, 200, 300, 400, 500, 600, 700, 800, 900, 1000 bp or more. In other embodiments, a subregion of a target nucleic acid has a length that is up to 10%, 20%, 30%, 40%, 50%, 60%, 70%, 80%, 90%, 95%, or more percent of a target nucleic acid length.

The skilled artisan will also appreciate that consideration is made, in the design of MIPs, for the relationship between probe length and target length. In some embodiments, MIPs are designed such that they are several hundred basepairs (e.g., up to 100, 200, 300, 400, 500, 600, 700, 800, 900, 1000 bp or more) longer than corresponding target (e.g., subregion of a target nucleic acid, target nucleic acid).

In some embodiments, lengths of subregions of a target nucleic acid may differ.

For example, if a target nucleic acid contains regions for which probe hybridization is not possible or inefficient, it may be necessary to use probes that capture subregions of one or more different lengths in order to avoid hybridization with problematic nucleic acids and capture nucleic acids that encompass a complete target nucleic acid.

Methods of the invention also provide for combining the method of fragmenting the nucleic acid prior to capture with other MIP capture techniques that are designed to increase target uniformity, reproducibility, and specificity. Other MIP capture techniques that can be conducted on fragmented genomic nucleic acids include methods discussed herein and in pending application, U.S. patent application Ser. No. 13/266,862, "Methods and Compositions for Evaluating Genetic Markers."

For example, multiple probes, e.g., MIPs, can be used to amplify each target nucleic acid. In some embodiments, the set of probes for a given target can be designed to 'tile' across the target, capturing the target as a series of shorter sub targets. In some embodiments, where a set of probes for a given target is designed to 'tile' across the target, some probes in the set capture flanking non-target sequence. Alternately, the set can be designed to 'stagger' the exact positions of the hybridization regions flanking the target, capturing the full target (and in some cases capturing flanking non-target sequence) with multiple probes having different targeting arms, obviating the need for tiling. The particular approach chosen will depend on the nature of the target set. For example, if small regions are to be captured, a staggered-end approach might be appropriate, whereas if longer regions are desired, tiling might be chosen. In all cases, the amount of bias-tolerance for probes targeting pathological loci can be adjusted ('dialed in') by changing the number of different MIPs used to capture a given molecule.

In some embodiments, the 'coverage factor', or number of probes used to capture a basepair in a molecule, is an important parameter to specify. Different numbers of probes per target are indicated depending on whether one is using the tiling approach or one of the staggered approaches.

Figure 2:
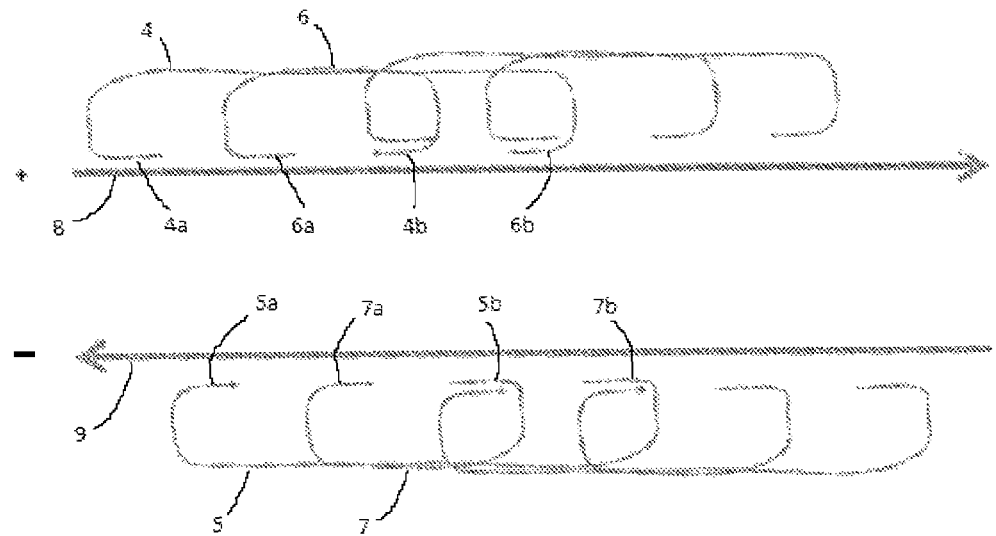
FIG. 2 is a schematic showing tiling of a nucleic acid template according to methods of the invention.

FIG. 2 illustrates a non-limiting embodiment of a tiled probe layout in which immediately adjacent probes hybridize to opposite strands of the nucleic acid template and probes on the same strand hybridize to the template in an overlapping manner.

Probes are immediately adjacent when they hybridize to a nucleic acid template in a manner in which a first targeting arm of a first probe and a first targeting arm of a second probe hybridize to a target without a targeting arm of a third probe hybridizing between the first targeting arm of the first probe and the first targeting arm of the second probe. FIG. 2 shows a plurality of molecular inversion probes, including a first molecular inversion probe 4, a second molecular inversion probe 5, a third molecular inversion probe 6 and a fourth molecular inversion probe 7. Probe 4 hybridizes to the plus strand 8 of the nucleic acid template and probe 5 hybridizes to the minus strand 9 of the nucleic acid template. Probe 4 has a targeting arm 4a and a targeting arm 4b. Probe 5 has a targeting arm 5a and a targeting arm 5b. The probes 4 and 5 are configured such that they hybridize to the target region in a manner in which targeting arm 4a of probe 4 is immediately adjacent to targeting arm 5a of probe 5. That is, probes 4 and 5 hybridize to the target region in a manner in which targeting arm 4a of probe 4 and targeting arm 5a of probe 5 hybridize to the target region without a targeting arm of a third probe (e.g., probe 6) being able to hybridize between targeting arm 4a of the probe 4 and targeting arm 5a of probe 5.

Probes are overlapping when they hybridize to a nucleic acid template in a manner in which two targeting arms of a first probe hybridize to a nucleic acid, and a first targeting arm of a second probe hybridizes to the nucleic acid at a location wholly or partially between the targeting arms of the first probe. Probes are also overlapping where the first targeting arm of a second probe hybridizes to a location on a nucleic acid that is wholly or partially the same location as a targeting arm of the first probe. FIG. 2 illustrates a non-limiting embodiment of a tiled probe layout in which probes on a target strand hybridize to the template in an overlapping manner. FIG. 2 shows probes 4-7 hybridized in a tiling manner to the plus strand 8 and the minus strand 9 of a nucleic acid template. Probe 4 includes targeting arms 4a and 4b. Probe 5 includes targeting arms 5a and 5b. Probe 6 includes targeting arms 6a and 6b. Probe 7 includes targeting arms 7a and 7b. On the plus strand 8, for example, probes 4 and 7 are configured such that targeting arm 6a of probe 6 hybridizes to a location on the plus strand 8 between targeting arm 4a and targeting arm 4b of probe 4. In that manner, probes 4 and 6 overlap with each other. Probe 6 is not immediately adjacent to probe 4, because there is a region between probes 4 and 6 in which a targeting arm of another probe (in this instance, targeting arm 5a of probe 5) can hybridize to the template. However, probe 6 provides overlapping coverage with probe 4, as explained above.

Similarly, on the minus strand 9, for example, probes 5 and 7 are configured such that targeting arm 7a of probe 7 hybridizes to the nucleic acid at a location between the targeting arm 5a and targeting arm 5b of probe 5. In that manner, probes 5 and 7 overlap with each other. Probe 7 is not immediately adjacent to probe 5, because there is a region between probes 5 and 7 in which a targeting arm of another probe (in this instance, targeting arm 6a of probe 6) can hybridize to the template. However, probe 7 provides overlapping coverage with probe 5, as explained above.

In the embodiment of FIG. 2, immediately adjacent probes hybridize to opposite strands, and so there is less competition between probes for a target region of a nucleic acid template, resulting in more capture events per targeted genomic region and increased capture efficiency. Also in this embodiment, probes on the same template hybridize in a manner in which their target regions overlap, resulting in greater coverage of the nucleic acid template.

In certain embodiments, a coverage factor of about 3 to about 10 is used. However, the methods are not so limited and coverage factors of up to 2, 3, 4, 5, 6, 7, 8, 9, 10, 20 or more may be used. It is to be appreciated that the coverage factor selected may depend on the probe layout being employed. For example, in the tiling approach, for a desired coverage factor, the number of probes per target is typically a function of target length, sub-target length, and spacing between adjacent sub-target start locations (step size). For example, for a desired coverage factor of 3, a 200 bp target with a start-site separation of 20 bp and sub-target length of 60 bp may be encompassed with 12 MIPs (FIG. 2). Thus, a specific coverage factor may be achieved by varying the number of probes per target nucleic acid and the length of the molecules captured. In the staggered approach, a fixed-length target nucleic acid is captured as several subregions or as 'super-targets', which are molecules comprising the target nucleic acid and additional flanking nucleic acids, which may be of varying lengths.

The coverage factor will be driven by the extent to which detection bias is tolerable. In some cases, where the bias tolerance is small, it may be desirable to target more subregions of target nucleic acid with, perhaps, higher coverage factors. In some embodiments, the coverage factor is up to 2, 3, 4, 5, 6, 7, 8, 9, 10 or more.

In some embodiments, when a tiled probe layout is used, when the target length is greater than 1 bp and when a step size (distance between the 5'-end of a target and the 5' end of its adjacent target) is less than the length of a target or subregion thereof, it is possible to compute probe number for a particular target based on target length (T), sub target length (S), and coverage factor (C), such that probe number=T/(S/C)+(C−1).

In some aspects, the disclosure provides methods to increase the uniformity of amplification efficiency when multiple molecules are amplified in parallel; methods to increase the reproducibility of amplification efficiency; methods to reduce the contribution of targeting probe variability to amplification efficiency; methods to reduce the effect on a given target nucleic acid of polymorphisms in probe hybridization regions; and/or methods to simplify downstream workflows when multiplex amplification by MIPs is used as a preparative step for analysis by nucleic acid sequencing.

Polymorphisms in the target nucleic acid under the regions flanking a target can interfere with hybridization, polymerase fill-in, and/or ligation. Furthermore, this may occur for only one allele, resulting in allelic drop-out, which ultimately decreases downstream sequencing accuracy. In some embodiments, using a set of MIPs having multiple hybridization sites for the capture of any given target, the probability of loss from polymorphism is substantially decreased because not all targeting arms in the set of MIPs will cover the location of the mutation.

Probes for MIP capture reactions may be synthesized on programmable microarrays because of the large number of sequences required. Because of the low synthesis yields of these methods, a subsequent amplification step is required to produce sufficient probe for the MIP amplification reaction. The combination of multiplex oligonucleotide synthesis and pooled amplification results in uneven synthesis error rates and representational biases. By synthesizing multiple probes for each target, variation from these sources may be averaged out because not all probes for a given target will have the same error rates and biases.

Multiplex amplification strategies disclosed herein may be used analytically, as in detection of SNPs, or preparatively, often for next-generation sequencing or other sequencing techniques. In the preparative setting, the output of an amplification reaction is generally the input to a shotgun library protocol, which then becomes the input to the sequencing platform. The shotgun library is necessary in part because next-generation sequencing yields reads significantly shorter than amplicons such as exons. In addition to the bias-reduction afforded by the multi-tiled approach described here, tiling also obviates the need for shotgun library preparation. Since the length of the capture molecule can be specified when the probes, e.g., MIPs, are designed, it can be chosen to match the read length of the sequencer. In this way, reads can 'walk' across an exon by virtue of the start position of each capture molecule in the probe set for that exon. Reducing analytical errors associated with bias in nucleic acid preparations:

In some embodiments, aspects of the invention relate to preparative steps in DNA sequencing-related technologies that reduce bias and increase the reliability and accuracy of downstream quantitative applications.

There are currently many genomics assays that utilize next-generation (polony-based) sequencing to generate data, including genome resequencing, RNA-seq for gene expression, bisulphite sequencing for methylation, and Immune-seq, among others. In order to make quantitative measurements (including genotype calling), these methods utilize the counts of sequencing reads of a given genomic locus as a proxy for the representation of that sequence in the original sample of nucleic acids. The majority of these techniques require a preparative step to construct a high-complexity library of DNA molecules that is representative of a sample of interest. This may include chemical or biochemical treatment of the DNA (e.g., bisulphite treatment), capture of a specific subset of the genome (e.g., padlock probe capture, solution hybridization), and a variety of amplification techniques (e.g., polymerase chain reaction, whole genome amplification, rolling circle amplification).

Systematic and random errors are common problems associated with genome amplification and sequencing library construction techniques. For example, genomic sequencing library may contain an over- or under-representation of particular sequences from a source genome as a result of errors (bias) in the library construction process. Such bias can be particularly problematic when it results in target sequences from a genome being absent or undetectable in the sequencing libraries. For example, an under representation of particular allelic sequences (e.g., heterozygotic alleles) from a genome in a sequencing library can result in an apparent homozygous representation in a sequencing library. As most downstream sequencing library quantification techniques depend on stochastic counting processes, these problems have typically been addressed by sampling enough (oversampling) to obtain a minimum number of observations necessary to make statistically significant decisions. However, the strategy of oversampling is generally limited to elimination of low-count Poisson noise, and the approach wastes resources and increases the expense required to perform such experiments. Moreover, oversampling can result in a reduced statistical confidence in certain conclusions (e.g., diagnostic calls) based on the data. Accordingly, new approaches are needed for overcoming bias in sequencing library preparatory methods.

Aspects of the disclosure are based, in part, on the discovery of methods for overcoming problems associated with systematic and random errors (bias) in genome capture, amplification and sequencing methods, namely high variability in the capture and amplification of nucleic acids and disproportionate representation of heterozygous alleles in sequencing libraries. Accordingly, in some embodiments, the disclosure provides methods that reduce variability in the capture and amplification of nucleic acids. In other embodiments, the methods improve allelic representation in sequencing libraries and, thus, improve variant detection outcomes. In certain embodiments, the disclosure provides preparative methods for capturing target nucleic acids (e.g., genetic loci) that involve the use of differentiator tag sequences to uniquely tag individual nucleic acid molecules. In some embodiments, the differentiator tag sequence permits the detection of bias based on the frequency with which pairs of differentiator tag and target sequences are observed in a sequencing reaction. In other embodiments, the methods reduce errors caused by bias, or the risk of bias, associated with the capture, amplification and sequencing of genetic loci, e.g., for diagnostic purposes.

Aspects of the invention relate to associating unique sequence tags (referred to as differentiator tag sequences) with individual target molecules that are independently captured and/or analyzed (e.g., prior to amplification or other process that may introduce bias). These tags are useful to distinguish independent target molecules from each other thereby allowing an analysis to be based on a known number of individual target molecules. For example, if each of a plurality of target molecule sequences obtained in an assay is associated with a different differentiator tag, then the target sequences can be considered to be independent of each other and a genotype likelihood can be determined based on this information. In contrast, if each of the plurality of target molecule sequences obtained in the assay is associated with the same differentiator tag, then they probably all originated from the same target molecule due to overrepresentation (e.g., due to biased amplification) of this target molecule in the assay. This provides less information than the situation where each nucleic acid was associated with a different differentiator tag. In some embodiments, a threshold number of independently isolated molecules (e.g., unique combinations of differentiator tag and target sequences) is analyzed to determine the genotype of a subject.

In some embodiments, the invention relates to compositions comprising pools (libraries) of preparative nucleic acids that each comprise "differentiator tag sequences" for detecting and reducing the effects of bias, and for genotyping target nucleic acid sequences. As used herein, a "differentiator tag sequence" is a sequence of a nucleic acid (a preparative nucleic acid), which in the context of a plurality of different isolated nucleic acids, identifies a unique, independently isolated nucleic acid. Typically, differentiator tag sequences are used to identify the origin of a target nucleic acid at one or more stages of a nucleic acid preparative method. For example, in the context of a multiplex nucleic acid capture reaction, differentiator tag sequences provide a basis for differentiating between multiple independent, target nucleic acid capture events. Also, in the context of a multiplex nucleic acid amplification reaction, differentiator tag sequences provide a basis for differentiating between multiple independent, primary amplicons of a target nucleic acid, for example. Thus, combinations of target nucleic acid and differentiator tag sequence (target:differentiator tag sequences) of an isolated nucleic acid of a preparative method provide a basis for identifying unique, independently isolated target nucleic acids.

It will be apparent to the skilled artisan that differentiator tags may be synthesized using any one of a number of different methods known in the art. For example, differentiator tags may be synthesized by random nucleotide addition.

Differentiator tag sequences are typically of a predefined length, which is selected to control the likelihood of producing unique target:differentiator tag sequences in a preparative reaction (e.g., amplification-based reaction, a circularization selection-based reaction, e.g., a MIP reaction). Differentiator tag sequences may be, up to 5, up to 6, up to 7 up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, or more nucleotides in length. For purposes of genotyping, isolated nucleic acids are identified as independently isolated if they comprise unique combinations of target nucleic acid and differentiator tag sequences, and observance of threshold numbers of unique combinations of target nucleic acid and differentiator tag sequences provide a certain statistical confidence in the genotype.

During a library preparation process, each nucleic acid molecule may be tagged with a unique differentiator tag sequence in a configuration that permits the differentiator tag sequence to be sequenced along with the target nucleic acid sequence of interest (the nucleic acid sequence for which the library is being prepared, e.g., a polymorphic sequence). The incorporation of the nucleic acid comprising a differentiator tag sequence at a particular step allows the detection and correction of biases in subsequent steps of the protocol.

A large library of unique differentiator tag sequences may be created by using degenerate, random-sequence polynucleotides of defined length. The differentiator tag sequences of the polynucleotides may be read at the final stage of the sequencing. The observations of the differentiator tag sequences may be used to detect and correct biases in the final sequencing read-out of the library. For example, the total possible number of differentiator tag sequences, which may be produced, e.g., randomly, is $4^N$, where N is the length of the differentiator tag sequence. Thus, it is to be understood that the length of the differentiator tag sequence may be adjusted such that the size of the population of MIPs having unique differentiator tag sequences is sufficient to produce a library of MIP capture products in which identical independent combinations of target nucleic acid and differentiator tag sequence are rare. As used herein combinations of target nucleic acid and differentiator tag sequences, may also be referred to as "target:differentiator tag sequences".

In the final readout of a sequencing process, each read may have an additional unique differentiator tag sequence. In some embodiments, when differentiator tag sequences are distributed randomly in a library, all the unique differentiator tag sequences will be observed about an equal number of times. Accordingly, the number of occurrences of a differentiator tag sequence may follow a Poisson distribution.

In some embodiments, overrepresentation of target:differentiator tag sequences in a pool of preparative nucleic acids (e.g., amplified MIP capture products) is indicative of bias in the preparative process (e.g., bias in the amplification process). For example, target:differentiator tag sequence combinations that are statistically overrepresented are indicative of bias in the protocol at one or more steps between the incorporation of the differentiator tag sequences into MIPs and the actual sequencing of the MIP capture products.

The number of reads of a given target:differentiator tag sequence may be indicative (may serve as a proxy) of the amount of that target sequence present in the originating sample. In some embodiments, the numbers of occurrence of sequences in the originating sample is the quantity of interest. For example, using the methods disclosed herein, the occurrence of differentiator tag sequences in a pool of MIPs may be predetermined (e.g., may be the same for all differentiator tag sequences). Accordingly, changes in the occurrence of differentiator tag sequences after amplification and sequencing may be indicative of bias in the protocol. Bias may be corrected to provide an accurate representation of the composition of the original MIP pool, e.g., for diagnostic purposes.

According to some aspects, a library of preparative nucleic acid molecules (e.g., MIPs, each nucleic acid in the library having a unique differentiator tag sequence, may be constructed such that the number of nucleic acid molecules in the library is significantly larger than the number prospective target nucleic acid molecules to be captured using the library. This ensures that products of the preparative methods include only unique target:differentiator tag sequence; e.g., in a MIP reaction the capture step would under sample the total population of unique differentiator tag sequences in the MIP library. For example, an experiment utilizing 1 ug of genomic DNA will contain about ~150,000 copies of a diploid genome. For a MIP library, each MIP in the library comprising a randomly produced 12-mer differentiator tag sequence (~1.6 million possible unique differentiator tag sequences), there would be more than 100 unique differentiator tag sequences per genomic copy. For a MIP library, each MIP in the library comprising a randomly produced 15-mer differentiator tag sequence (~1 billion possible unique differentiator tag sequences), there would be more than 7000 unique differentiator tag sequences per genomic copy. Therefore, the probability of the same differentiator tag sequence being incorporated multiple times is incredibly small. Thus, it is to be appreciated that the length of the differentiator tag sequence is to be selected based on the amount of target sequence in a MIP capture reaction and the desired probability for having multiple, independent occurrences of target:differentiator tag sequence combinations.

The skilled artisan will appreciate that as part of a MIP library preparation process, adapters may be ligated onto the ends of the molecules of interest. Adapters often contain PCR primer sites (for amplification or emulsion PCR) and/or sequencing primer sites. In addition, barcodes may be included, for example, to uniquely identify individual samples (e.g., patient samples) that may be mixed together. (See, e.g., USPTO Publication Number US 2007/0020640 A1 (McCloskey et al.)

The actual incorporation of the random differentiator tag sequences can be performed through various methods known in the art. For example, nucleic acids comprising differentiator tag sequences may be incorporated by ligation. This is a flexible method, because molecules having differentiator tag sequence can be ligated to any blunt-ended nucleic acids. The sequencing primers must be incorporated subsequently such that they sequence both the differentiator tag sequence and the target sequence. Alternatively, the sequencing adaptors can be synthesized with the random differentiator tag sequences at their 3' end (as degenerate bases), so that only one ligation must be performed. Another method is to incorporate the differentiator tag sequence into a PCR primer, such that the primer structure is arranged with the common adaptor sequence followed by the random differentiator tag sequence followed by the PCR priming sequence (in 5' to 3' order). A differentiator tag sequence and adaptor sequence (which may contain the sequencing primer site) are incorporated as tags. Another method to incorporate the differentiator tag sequences is to synthesize them into a padlock probe prior to performing a gene capture reaction. The differentiator tag sequence is incorporated 3' to the targeting arm but 5' to the amplification primer that will be used downstream in the protocol. Another method to incorporate the differentiator tag sequences is as a tag on a gene-specific or poly-dT reverse-transcription primer. This allows the differentiator tag sequence to be incorporated directly at the cDNA level.

In some embodiments, at the incorporation step, the distribution of differentiator tag sequences can be assumed to be uniform. In this case, bias in any part of the protocol would change the uniformity of this distribution, which can be observed after sequencing. This allows the differentiator tag sequence to be used in any preparative process where the ultimate output is sequencing of many molecules in parallel.

Differentiator tag sequences may be incorporated into probes (e.g., MIPs) of a plurality when they are synthesized on-chip in parallel, such that degeneracy of the incorporated nucleotides is sufficient to ensure near-uniform distribution in the plurality of probes. It is to be appreciated that amplification of a pool of unique differentiator tag sequences may itself introduce bias in the initial pool. However, in most practical cases, the scale of synthesis (e.g., by column synthesis, chip based synthesis, etc.) is large enough that amplification of an initial pool of differentiator tag sequences is not necessary. By avoiding amplification or selection steps on the pool of unique differentiator tag sequences, potential bias may be minimized.

One example of the use of the differentiator tag sequences is in genome resequencing. Considering that the raw accuracy of most next-generation sequencing instruments is relatively low, it is crucial to oversample the genomic loci of interest.

Furthermore, since there are two alleles at every locus, it is important to sample enough to ensure that both alleles have been observed a sufficient number of times to determine with a sufficient degree of statistical confidence whether the sample is homozygous or heterozygous. Indeed, the sequencing is performed to sample the composition of molecules in the originating sample. However, after multiple reads have been collected for a given locus, it is possible that due to bias (e.g., caused by PCR amplification steps), a large fraction of the reads are derived from a single originating molecule. This would skew the population of target sequences observed, and would affect the outcome of the genotype call. For example, it is possible that a locus that is heterozygous is called as homozygous, because there are only a few observations of the second allele out of many observations of that locus. However, if information is available on differentiator tag sequences, this situation could be averted, because the overrepresented allele would be seen to also have an over-represented differentiator tag sequence (i.e., the sequences with the overrepresented differentiator tag sequence all originated from the same single molecule). Therefore, the sequences and corresponding distribution of differentiator tag sequences can be used as an additional input to the genotype-calling algorithm to significantly improve the accuracy and confidence of the genotype calls.

Barcode Sequences

In certain embodiments, at least one barcode sequence is attached to or incorporated into the isolated probes prior to sequencing. Strategies for barcoding nucleic acid templates are described for example in Porreca et al. (U.S. patent application Ser. No. 13/081,660) and Umbarger et al. (U.S. patent application Ser. No. 13/081,660), the content of each of which is incorporated by reference herein in its entirety. In embodiments that use more than one barcode, the barcode sequences may be attached to the template such that a first barcode sequence is attached to a 5' end of the template and a second barcode sequence is attached to a 3' end of the template. The first and second barcode sequences may be the same, or they may be different. Barcode sequence may be incorporated into a contiguous region of a template that includes the target to be sequenced.

Exemplary methods for designing sets of barcode sequences and other methods for attaching barcode sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety.

The barcode sequence generally includes certain features that make the sequence useful in sequencing reactions. For example the barcode sequences can be designed to have minimal or no homopolymer regions, i.e., 2 or more of the same base in a row such as AA or CCC, within the barcode sequence. The barcode sequences can also be designed so that they do not overlap the target region to be sequence or contain a sequence that is identical to the target.

The first and second barcode sequences are designed such that each pair of sequences is correlated to a particular sample, allowing samples to be distinguished and validated. Methods of designing sets of barcode sequences is shown for example in Brenner et al. (U.S. Pat. No. 6,235,475), the contents of which are incorporated by reference herein in their entirety. In certain embodiments, the barcode sequences range from about 2 nucleotides to about 50; and preferably from about 4 to about 20 nucleotides. Since the barcode sequence is sequenced along with the template nucleic acid or may be sequenced in a separate read, the oligonucleotide length should be of minimal length so as to permit the longest read from the template nucleic acid attached. Generally, the barcode sequences are spaced from the template nucleic acid molecule by at least one base.

Methods of the invention involve attaching the barcode sequences to the template nucleic acids. Template nucleic acids are able to be fragmented or sheared to desired length, e.g. generally from 100 to 500 bases or longer, using a variety of mechanical, chemical and/or enzymatic methods. DNA may be randomly sheared via sonication, exposed to a DNase or one or more restriction enzymes, a transposase, or nicking enzyme. RNA may be fragmented by brief exposure to an RNase, heat plus magnesium, or by shearing. The RNA may be converted to cDNA before or after fragmentation.

Barcode sequence is integrated with template using methods known in the art. Barcode sequence is integrated with template using, for example, a ligase, a polymerase, Topo cloning (e.g., Invitrogen's topoisomerase vector cloning system using a topoisomerase enzyme), or chemical ligation or conjugation. The ligase may be any enzyme capable of ligating an oligonucleotide (RNA or DNA) to the template nucleic acid molecule. Suitable ligases include T4 DNA ligase and T4 RNA ligase (such ligases are available commercially, from New England Biolabs). Methods for using ligases are well known in the art. The polymerase may be any enzyme capable of adding nucleotides to the 3' and the 5' terminus of template nucleic acid molecules. Barcode sequence can be incorporated via a PCR reaction as part of the PCR primer.

The ligation may be blunt ended or via use of overhanging ends. In certain embodiments, following fragmentation, the ends of the fragments may be repaired, trimmed (e.g. using an exonuclease), or filled (e.g., using a polymerase and dNTPs), to form blunt ends. Upon generating blunt ends, the ends may be treated with a polymerase and dATP to form a template independent addition to the 3'-end and the 5-end of the fragments, thus producing a single A overhanging. This single A is used to guide ligation of fragments with a single T overhanging from the 5'-end in a method referred to as T-A cloning.

Alternatively, because the possible combination of overhangs left by the restriction enzymes are known after a restriction digestion, the ends may be left as is, i.e., ragged ends. In certain embodiments double stranded oligonucleotides with complementary over hanging ends are used.

Amplification

Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyperbranched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other, and therefore, this length is a controllable parameter.

With PCR, it is possible to amplify a single copy of a specific target sequence in genomic DNA to a level that can be detected by several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences can be used to obtain segments of DNA (e.g., genes) for insertion into recombinant vectors.

Methods for performing PCR in droplets are shown for example in Link et al. (U.S. patent application numbers 2008/0014589, 2008/0003142, and 2010/0137163) and Anderson et al. (U.S. Pat. No. 7,041,481 and which reissued as RE41,780), the content of each of which is incorporated by reference herein in its entirety.

Other amplification methods and strategies can also be utilized to detect nucleic acids in biological fluids. For example, another approach would be to combine PCR and the ligase chain reaction (LCR). Since PCR amplifies faster than LCR and requires fewer copies of target DNA to initiate, PCR can be used as first step followed by LCR. The amplified product could then be used in a LCR or ligase detection reaction (LDR) in an allele-specific manner that would indicate if a mutation was present. Another approach is to use LCR or LDR for both amplification and allele-specific discrimination. The later reaction is advantageous in that it results in linear amplification. Thus the amount of amplified product is a reflection of the amount of target DNA in the original specimen and therefore permits quantitation.

LCR utilizes pairs of adjacent oligonucleotides which are complementary to the entire length of the target sequence (Barany F. (1991) PNAS 88:189-193; Barany F. (1991) PCR Methods and Applications 1:5-16). If the target sequence is perfectly complementary to the primers at the junction of these sequences, a DNA ligase will link the adjacent 3' and 5' terminal nucleotides forming a combined sequence. If a thermostable DNA ligase is used with thermal cycling, the combined sequence will be sequentially amplified. A single base mismatch at the junction of the oligonucleotides will preclude ligation and amplification. Thus, the process is allele-specific. Another set of oligonucleotides with 3' nucleotides specific for the mutant would be used in another reaction to identify the mutant allele. A series of standard conditions could be used to detect all possible mutations at any known site. LCR typically utilizes both strands of genomic DNA as targets for oligonucleotide hybridization with four primers, and the product is increased exponentially by repeated thermal cycling.

A variation of the reaction is the ligase detection reaction (LDR) which utilizes two adjacent oligonucleotides which are complementary to the target DNA and are similarly joined by DNA ligase (Barany F. (1991) PNAS 88:189-193). After multiple thermal cycles the product is amplified in a linear fashion. Thus the amount of the product of LDR reflects the amount of target DNA. Appropriate labeling of the primers allows detection of the amplified product in an allele-specific manner, as well as quantitation of the amount of original target DNA. One advantage of this type of reaction is that it allows quantitation through automation (Nickerson et al. (1990) PNAS 87: 8923-8927).

Sequencing

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton ($H^+$), which signal detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Probe Hybridization

In certain embodiments, captured and amplified target are detected using detectably labeled probes. In particular embodiments, the detectably labeled probes are optically labeled probes, such as fluorescently labeled probes. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels.

During amplification, fluorescent signal is generated in a TaqMan assay by the enzymatic degradation of the fluorescently labeled probe. The probe contains a dye and quencher that are maintained in close proximity to one another by being attached to the same probe. When in close proximity, the dye is quenched by fluorescence resonance energy transfer to the quencher. Certain probes are designed that hybridize to the wild-type of the target, and other probes are designed that hybridize to a variant of the wild-type of the target. Probes that hybridize to the wild-type of the target have a different fluorophore attached than probes that hybridize to a variant of the wild-type of the target. The probes that hybridize to a variant of the wild-type of the target are designed to specifically hybridize to a region in a PCR product that contains or is suspected to contain a single nucleotide polymorphism or small insertion or deletion.

During the PCR amplification, the amplicon is denatured allowing the probe and PCR primers to hybridize. The PCR primer is extended by Taq polymerase replicating the alternative strand. During the replication process the Taq polymerase encounters the probe which is also hybridized to the same strand and degrades it. This releases the dye and quencher from the probe which are then allowed to move away from each other. This eliminates the FRET between the two, allowing the dye to release its fluorescence. Through each cycle of cycling more fluorescence is released. The amount of fluorescence released depends on the efficiency of the PCR reaction and also the kinetics of the probe hybridization. If there is a single mismatch between the probe and the target sequence the probe will not hybridize as efficiently and thus a fewer number of probes are degraded during each round of PCR and thus less fluorescent signal is generated. This difference in fluorescence per droplet can be detected and counted. The efficiency of hybridization can be affected by such things as probe concentration, probe ratios between competing probes, and the number of mismatches present in the probe.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for analyzing a nucleic acid template, the method comprising:
   obtaining a sample comprising a nucleic acid template;
   fragmenting the nucleic acid template to produce a plurality of fragments;
   tiling a plurality of molecular inversion probes across a portion of at least one of the fragments, wherein immediately adjacent probes hybridize to opposite strands of the at least one fragment and probes on the same strand hybridize to the at least one fragment in an overlapping manner;
   filling-in a region between targeting arms of a plurality of the molecular inversion probes with nucleotides; and
   analyzing the filled-in region of a plurality of the probes to obtain sequence information about the at least one fragment, thereby obtaining sequence information about the nucleic acid template.

2. The method according to claim 1, wherein analyzing is by sequencing.

3. The method according to claim 2, wherein prior to sequencing, the method further involves amplifying the filled-in region of the plurality of the probes.

4. The method according to claim 2, wherein sequencing is sequencing-by-synthesis.

5. The method according to claim 4, wherein sequencing-by-synthesis is single molecule sequencing-by-synthesis.

6. The method according to claim 2, wherein sequencing information comprises a mutation in the nucleic acid sequence.

7. The method according to claim 6, wherein the mutation is selected from the group consisting of: a single nucleotide polymorphism (SNP), an insertion, a deletion, an inversion, a translocation, a substitution, and a combination thereof.

8. The method according to claim 1, wherein the filling-in step uses a ligase.

9. The method according to claim 1, wherein the filling-in step uses a polymerase.

10. The method according to either claim 8 or 9, wherein a ligase is used to covalently link the filled-in region to one of the targeting arms.

11. The method according to claim 2, wherein prior to sequencing, a barcode is attached to the molecular inversion probe.

12. The method according to claim 2, wherein prior to sequencing, a sequencing adaptor is attached to the molecular inversion probe.

13. The method according to claim 2, wherein prior to sequencing, a barcode and a sequencing adaptor are attached to the molecular inversion probe.

14. The method according to claim 2, wherein prior to sequencing, the molecular inversion probe is attached to a solid surface.

15. The method according to claim 14, wherein the surface is a surface of a flow cell.

\* \* \* \* \*